US012653588B2

(12) United States Patent
Ahmadi et al.

(10) Patent No.: US 12,653,588 B2
(45) Date of Patent: Jun. 16, 2026

(54) EXPANDABLE IMPLANT, IMPLANT SYSTEM, KIT OF PARTS FOR ASSEMBLING AN EXPANDABLE IMPLANT, AND METHOD OF PLACING AN IMPLANT IN A BONE

(71) Applicant: AM Solutions Holding B.V., The Hague (NL)

(72) Inventors: Seyed Mohammad Ahmadi, The Hague (NL); Banafsheh Sajadi, The Hague (NL); Sanne Aarts, The Hague (NL)

(73) Assignee: AM Solutions Holding B.V., The Hague (NL)

( * ) Notice: Subject to any disclaimer, the term of this patent is extended or adjusted under 35 U.S.C. 154(b) by 323 days.

(21) Appl. No.: 18/016,566

(22) PCT Filed: Jul. 15, 2021

(86) PCT No.: PCT/NL2021/050446
§ 371 (c)(1),
(2) Date: Jan. 17, 2023

(87) PCT Pub. No.: WO2022/025759
PCT Pub. Date: Feb. 3, 2022

(65) Prior Publication Data
US 2023/0301695 A1      Sep. 28, 2023

(30) Foreign Application Priority Data
Jul. 27, 2020     (NL) ...................................... 2026145

(51) Int. Cl.
*A61B 17/84*          (2006.01)
*A61B 17/56*          (2006.01)

(52) U.S. Cl.
CPC ...... *A61B 17/844* (2013.01); *A61B 2017/564* (2013.01)

(58) Field of Classification Search
CPC .......................... A61B 17/844; A61B 17/8858
See application file for complete search history.

(56) References Cited

U.S. PATENT DOCUMENTS 6,127,597 A    10/2000 Beyar et al.
8,535,380 B2    9/2013 Greenhalgh et al.
(Continued)

FOREIGN PATENT DOCUMENTS

DE    10 2015 110 B3    6/2016
EP    3 092 976 A1    11/2016
(Continued)

OTHER PUBLICATIONS

International Search Report and Written Opinion for International Application No. PCT/NL2021/050446, mailed Oct. 1, 2021.
(Continued)

*Primary Examiner* — Olivia C Chang
(74) *Attorney, Agent, or Firm* — Wolf, Greenfield & Sacks, P.C.

(57) ABSTRACT

An expandable implant (1) implantable in an intra-osseous cavity of a bone comprises an anchoring body (2) having a distal end and a proximal end for anchoring the distal end relative to a part of the bone outside the cavity. An expandable part (4), for in the intra¬osseous cavity, is fixated to the anchoring body, e.g. at the distal end. The expandable part comprises a movable piece with a load supporting surface for supporting a wall of the cavity against a load acting on the bone. The movable piece is movable away from the anchoring body in a direction of expansion perpendicular to the longitudinal direction, to bring the load supporting surface from an initial position in a non-expanded state to an expanded position in a expanded state in which the load supporting surface abuts to the wall. A driving part (70) is movable relative to the proximal end of the anchoring body. A transmission (73) extends between the driving part and the (Continued)

expandable part, the transmission engaging on the load supporting surface for transferring at least a part of a force exerted on the driving part to move the driving part relative to the proximal end of the anchoring body to the load supporting surface and thereby actuate movement of the load supporting surface in the direction of expansion.

14 Claims, 8 Drawing Sheets

(56) References Cited

U.S. PATENT DOCUMENTS

| | | | |
|---|---|---|---|
| 8,974,507 | B2 | 3/2015 | Eisermann |
| 8,986,349 | B1 | 3/2015 | German et al. |
| 10,238,443 | B2 | 3/2019 | Seifert et al. |
| 2003/0004575 | A1 | 1/2003 | Erickson |
| 2005/0278036 | A1 | 12/2005 | Leonard et al. |
| 2006/0111715 | A1 | 5/2006 | Jackson |
| 2006/0212118 | A1 | 9/2006 | Abernathie |
| 2006/0287725 | A1 | 12/2006 | Miller |
| 2007/0173826 | A1 | 7/2007 | Canaveral et al. |
| 2008/0195159 | A1 | 8/2008 | Kloss et al. |
| 2009/0024217 | A1 | 1/2009 | Levy et al. |
| 2009/0292361 | A1* | 11/2009 | Lopez ..................... A61F 2/446 |
| | | | 623/17.15 |
| 2010/0211114 | A1 | 8/2010 | Jackson |
| 2010/0292796 | A1 | 11/2010 | Greenhalgh et al. |
| 2011/0106174 | A1 | 5/2011 | Rezach |
| 2011/0112578 | A1 | 5/2011 | Keiser et al. |
| 2012/0010668 | A1 | 1/2012 | Shimko |
| 2013/0197647 | A1 | 8/2013 | Wolters et al. |
| 2013/0211458 | A1 | 8/2013 | Rezach |
| 2014/0236297 | A1 | 8/2014 | Iott et al. |
| 2014/0277501 | A1 | 9/2014 | Northcutt et al. |
| 2016/0317188 | A1* | 11/2016 | Oglaza ............... A61B 17/1671 |
| 2017/0354513 | A1 | 12/2017 | Maglaras et al. |
| 2018/0078384 | A1 | 3/2018 | Suddaby |
| 2018/0296361 | A1 | 10/2018 | Butler et al. |
| 2019/0053912 | A1 | 2/2019 | Suddaby |
| 2019/0083275 | A1 | 3/2019 | Bell et al. |
| 2019/0175224 | A1 | 6/2019 | Doubler et al. |
| 2019/0274838 | A1 | 9/2019 | Manwill et al. |
| 2020/0093603 | A1 | 3/2020 | Manwill et al. |
| 2022/0142783 | A1 | 5/2022 | Ahmadi |
| 2022/0168113 | A1 | 6/2022 | Ahmadi et al. |
| 2024/0138883 | A1 | 5/2024 | Ahmadi et al. |
| 2025/0241763 | A1 | 7/2025 | Ahmadi et al. |
| 2025/0275855 | A1 | 9/2025 | Ahmadi et al. |

FOREIGN PATENT DOCUMENTS

| | | |
|---|---|---|
| EP | 3 463 202 A1 | 4/2019 |
| JP | 2003-530915 A | 10/2003 |
| JP | 2004-522469 A | 7/2004 |
| JP | 2008-520269 A | 6/2008 |
| JP | 2011-520580 A | 7/2011 |
| JP | 2012-509157 A | 4/2012 |
| JP | 2018-526152 A | 9/2018 |
| WO | WO 01/54598 A1 | 8/2001 |
| WO | WO 01/78798 A1 | 10/2001 |
| WO | WO 02/38062 A2 | 5/2002 |
| WO | WO 2006/051547 A2 | 5/2006 |
| WO | WO 2009/147527 A2 | 12/2009 |
| WO | WO 2010/059866 A1 | 5/2010 |
| WO | 2012/162551 A2 | 11/2012 |
| WO | 2012/162551 A3 | 11/2012 |
| WO | WO 2016/112175 A1 | 7/2016 |
| WO | WO 2017/042366 A1 | 3/2017 |
| WO | WO 2017/192525 A1 | 11/2017 |
| WO | WO 2017/201371 A1 | 11/2017 |
| WO | WO 2018/163056 A1 | 9/2018 |

OTHER PUBLICATIONS

International Preliminary Report on Patentability in International Application No. PCT/NL2021/050446, mailed Feb. 9, 2023.
Patrick et al., Robust sacrificial polymer templates for 3D interconnected microvasculature in fiber-reinforced composites. Composites Part A: Applied Science and Manufacturing. Sep. 1, 2017;100:361-70.
Sun et al., Bio-CAD modeling and its applications in computer-aided tissue engineering. Computer-aided design. Sep. 15, 2005;37(11):1097-114.
Wang et al., Interlocking assembled 3D auxetic cellular structures. Materials & Design. Jun. 5, 2016;99:467-76.
International Search Report and Written Opinion for International Application No. PCT/NL2022/050133, mailed Apr. 25, 2022.

* cited by examiner

EXPANDABLE IMPLANT, IMPLANT SYSTEM, KIT OF PARTS FOR ASSEMBLING AN EXPANDABLE IMPLANT, AND METHOD OF PLACING AN IMPLANT IN A BONE

CROSS-REFERENCE TO RELATED APPLICATIONS

This application is a national stage filing under 35 U.S.C. § 371 of International Patent Application Serial No. PCT/NL2021/050446, filed Jul. 15, 2021, which claims priority to Netherlands application number 2026145 filed Jul. 27, 2020, each of which is incorporated herein by reference in its entirety.

FIELD OF THE INVENTION

This invention relates to expandable implants which are in-vivo implantable in an intra-osseous cavity of a bone, such as a vertebra, of a human or non-human mammal to provide support to the bone, such as for a vertebra. In particular, but not limited thereto, the invention relates to expandable implants such as useable in percutaneous osteoplasty, vertebroplasty and kyphoplasty. The invention further relates to implant systems, kits of parts for assembling expandable implants, and methods of placing such implants.

BACKGROUND OF THE INVENTION

Trauma and other conditions, like osteoporosis, can lead to parts of bone tissue being weakened, and cause fracture or collapse of the bone. To stabilize the bone and transfer mechanical loads, percutaneous osteoplasty, the injection of bone cements, to stabilize and provide support to the bone is known. Various types of bones may need such stabilization and support.

For example, vertebral body compression fractures frequently result in severe and disabling back pain. Many patients may experience decreased quality of life due to severe pain, prolonged immobilization, kyphosis, pulmonary deterioration, depression, and loss of independence. The most common cause is believed to be osteoporosis, more than 700,000 osteoporosis-related fractures are diagnosed each year in the United States alone. Other causes include primary and metastatic malignancies, trauma, hemangioma, and osteonecrosis. Since medical therapy, such as exercise, physio-therapy, etc. may not provide sufficient or no results in alleviating the symptoms, surgery may be needed. Vertebroplasty has become a widely used alternative surgical treatment for symptomatic such fractures of which the symptoms cannot be treated by medical therapy. Vertebroplasty is a minimally invasive image-guided procedure involving the injection of bone cement into a vertebral body fracture in an effort to reduce pain and improve stability of the fracture. Kyphoplasty is a similar procedure, but utilizes an inflatable balloon in an effort to reduce the fracture and create a cavity to theoretically allow safer injection of cement into the fractured vertebral body.

It is known to use in these procedures a vertebral body stent which is expanded in the cavity to prevent the vertebral body from collapsing until the bone cement has hardened. These commonly known stents are expandable mesh-wire tubular structures similar to those used in angioplastic stents, which upon expansion remain in position and expand by changing the shape of the structure to increase the diameter of the mesh. These stents are themselves are not capable of withstanding the compressive load acting on the vertebral column. For stabilization and support of the vertebra, the bone cement is thus required. However, these known solutions tend to lack a sufficient anchoring and there is a risk that the structure formed by the stent and the hardened bone cement is displaced relative to the vertebra.

From United States patent application publication US 2007/0173826 an Intramedullar Reduction/Fixation Device is known. The device comprises a hollow extender tube through which an extension rod traverses. The device has flexible blades of which the ends at one side can be pushed away from one another by a movement of the extension rod, while the ends at the other side remain in position, so as to flex the blades and bring a part thereof into contact with bone surfaces in a medullar cavity. The hollow extender tube is provided with fins or keels which extend in the axial direction of the tube to stabilize the device in the bone. However, although these fins or keels help to resist rotation of the extender tube upon a rotational movement of the extension rod, the device itself is not anchored in the bone and can be removed by simple closing the flexible blades, as is disclosed in this prior art document.

For vertebrae, it is known from United States patent application publication US 2016/0317188 to anchor an intra-vertebral implant in the pedicle. This prior art document discloses an expandable intravertebral implant system which is fixated to the pedicle.

The system comprises two separate parts: an intravertebral implant and a pedicle fixation. The implant is loosely coupled to the pedicle fixation, with the posterior part of the implant slideably admitted in a cannula through the pedicle fixation. The implant can thereby freely move in rotation around, and in translation along, the main axis of the pedicle fixation but is secured in all other directions. At the same time, the implant can be expanded with an instrument by an access via the cannula.

The intravertebral implant itself has an expandable anterior part, which consists of opposite plates, forming respective bearing surfaces in the vertebral body upon expansion of the implant. The anterior part also comprises a central traction tube suitable for controlling the expansion. The posterior part of the implant consists of a hollow cylindrical body in which the central traction tube can slide to expand the implant. Via the cannula the instrument can pull the central traction tube relative to the cylindrical body. This results in the central traction tube sliding in the cylindrical body, thereby causing the expansion of the intravertebral implant. After expansion, the implant can be stabilized by injecting bone cement.

However, a disadvantage of this system is that the implant has a relatively high risk of failure because expanding is mechanically complex, with a significant amount of movable parts, each of which bears a risk of getting stuck and therefore blocking expansion of the implant.

SUMMARY OF THE INVENTION

The present invention provides expandable implants, implant systems, kits of parts for assembling an expandable implant, and methods as described in the accompanying claims.

Specific embodiments of the invention are set forth in the dependent claims.

These and other aspects of the invention will be apparent from and elucidated with reference to the embodiments described hereinafter.

BRIEF DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION OF THE PREFERRED EMBODIMENTS

Figure 1:
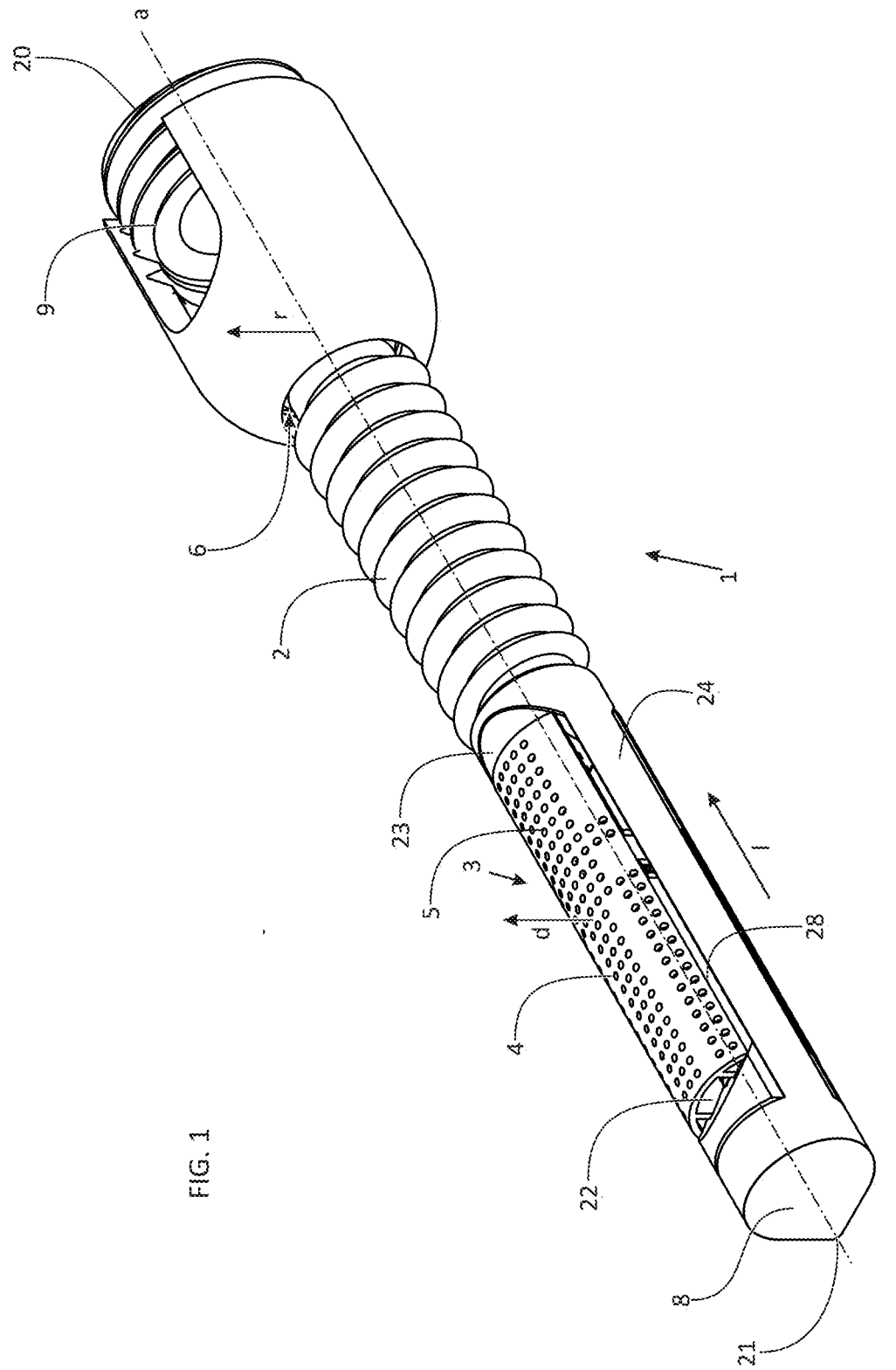
FIG. 1 schematically shows a perspective view of an example of an embodiment of an expandable implant in a non-expanded state.

Herein below, details will not be explained in any greater extent than considered necessary for the understanding and appreciation of the underlying concepts of the present invention, in order not to obfuscate or distract from the teachings of the present invention.

Referring to FIGS. 1-5 an example of an implant 1 for in-vivo implantation in a human or non-human mammalian body is shown. The shown example can e.g. be assembled from a kit as shown in FIGS. 6-7. The implant can be used in a surgical procedure, in which an incision is made in the mammalian body; the implant is implanted into the mammalian body; and is anchored in bone of the mammalian body. Although the implant can be implemented to be anchored into cancellous bone, in the following examples are described in which the implant is anchored into cortical bone.

The implant 1 may be implemented, e.g. by appropriate dimensioning of the length, diameter, expansion ratio, and porosity, to be suitable for any type of bone of the mammalian body. The shown example is dimensioned to be implanted in an intra-osseous cavity of a bone, such as a vertebra, of a human or non-human mammal. The cavity may be a void present in the bone prior to surgery or a cavity created by a medical practitioner specifically for the implantation of the implant. The implant can for example be a vertebral, such as lumbar, thoracic or sacral vertebral implant.

Typical dimensions of the implant 1 (although other sizes being possible as well depending on the cavity in which the device is to be placed) can be a length between 25 mm to 65 mm. For example, the length can be 25 mm or more, such as 35 mm or more. The length can be less than 65 mm, for example less than 60 mm, for instance 40 mm or less. A currently preferred range for the length is a length between 40 and 60 mm. A typical maximum, non-expanded diameter can for example be less than 10 mm, such as less than 8 mm, such as 5 mm or less. Preferably, but not necessarily, that diameter is 1 mm or more, such as 1.5 mm or more. 2.25 mm or more, such as 3 mm or more. A typical maximum expansion of the device is for example between 1.5 and 4 times the non-expanded diameter. Other maximum expansions are likewise possible, and it is currently preferred that the maximum expansion is less than 5 times the non-expanded diameter which ensures a mechanical stable and reliable expansion.

As shown, the implant may comprise an anchoring body 2 with a distal end 21 and a proximal end 20, at a distance from the distal end 21. Here, the term "distal" is used in the sense that after implantation the distal end 21 lies the deepest into the bone, and the proximal end 20 is then closer to, preferably at, or projecting outwards from, the bone surface. The anchoring body 2 serves to anchor the implant in a part of a bone, e.g. in the pedicle. When anchored, the anchoring body 2 resists forces in the distal-proximal direction. The anchoring body 2 then inhibits or blocks translational movements of the implant 1 relative to the bone part in which the anchoring body is anchored, at least in the in the distal-proximal direction, and, optionally, inhibits or blocks rotational movements around an axis extending in the distal-proximal direction as well. In addition, the bone part may surround the anchoring part of the anchoring body such that translational forces perpendicular to the distal-proximal direction or rotational forces around an axis perpendicular to the distal-proximal direction are resisted as well.

The implant 1 has an expandable part 3 to be admitted in the intra-osseous cavity. The expandable part 3 has in this example no degrees of freedom relative to the anchoring body 2. A movement of the anchoring body 2 thus moves the expandable part 3. This allows a precise positioning and orientation of the expandable part 3 in the cavity. As explained below in more detail, the expandable part is fixated to the anchoring body, more specifically to the distal end 21, and has an expanded state and a non-expanded state. Thus, the expandable part is unmovable relative to the anchoring body and a movement of the anchoring body 2 leads to the same movement of the expandable part, which provides a direct handling and facilitates positioning and orientation by the medical practitioner.

The expandable part 3 may comprise one, two or more movable pieces 4, such as a plate or a bulk block, each with a load supporting surface 5 for supporting a wall of the intra-osseous cavity against a load acting on the bone. The movable piece 4 is movable away from the anchoring body 2 in a direction of expansion d. This direction of expansion d is in this example perpendicular to the longitudinal direction l, from the distal end 21 towards the proximal end 20. The displacement of the movable piece 4 brings the load supporting surface 5 from an initial position, that is in the non-expanded state, shown in FIGS. 1-3 to an expanded position in the expanded state, shown in FIGS. 2,4 and 5. When correctly positioned in the cavity, the load supporting surface 5 then abuts to the wall of the intra-osseous cavity and supports the bone matter from which the wall is made, e.g. against a load acting thereon from outside the bone, such as a compressive load acting on an outside surface of the bone in a direction opposite to the direction of expansion.

Although the implant does not need to be expanded to the fullest extent, in the shown example displacement of the load supporting surface 5 is constrained to a limited range, the limited range being between the initial position and a maximally expanded position, and the position is infinitely adjustable between the initial position and the maximally expanded position by a suitable actuation of the movement, as will be apparent from the below.

The implant 1 further has a drive part 6, which is located at the proximal end 20 of the anchoring body 2 in this example. The drive part 6 is arranged to drive expansion of the expandable part at a selected point in time, in this example after anchoring the implant 1 in the bone. While anchoring the implant, the load supporting surfaces 5 are positioned and oriented as deemed suitable in the cavity by a medical practitioner. Thus, prior to expansion the implant 1 is already anchored, with the expandable part 3 in the non-expanded state oriented and position to after expansion support the bone as deemed suitable by the medical practitioner. The drive part 6 is movable relative to the proximal end 20 of the anchoring body 2, e.g. can be pushed towards, pulled away from or, as indicated with arrow A1 in FIG. 5, in this example rotated relative to the proximal end 20. This movement of the drive part 6 drives expansion of the expandable part 3. In this example, the expandable part is unmovable relative to the anchoring body, and this movement of the drive part 6 can therefore not result in change in position or orientation of the expandable part 3 relative to the anchoring body. It will be apparent though, that adjustments may be made in the position or orientation of the expandable part 3 after (partial) expansion, e.g. by reducing the expansion and then manipulating the anchoring body 2 to e.g. extend deeper or less deep into the bone and/or to rotate the anchoring body around a longitudinal axis to change the orientation of the expandable part 3.

Figure 2:
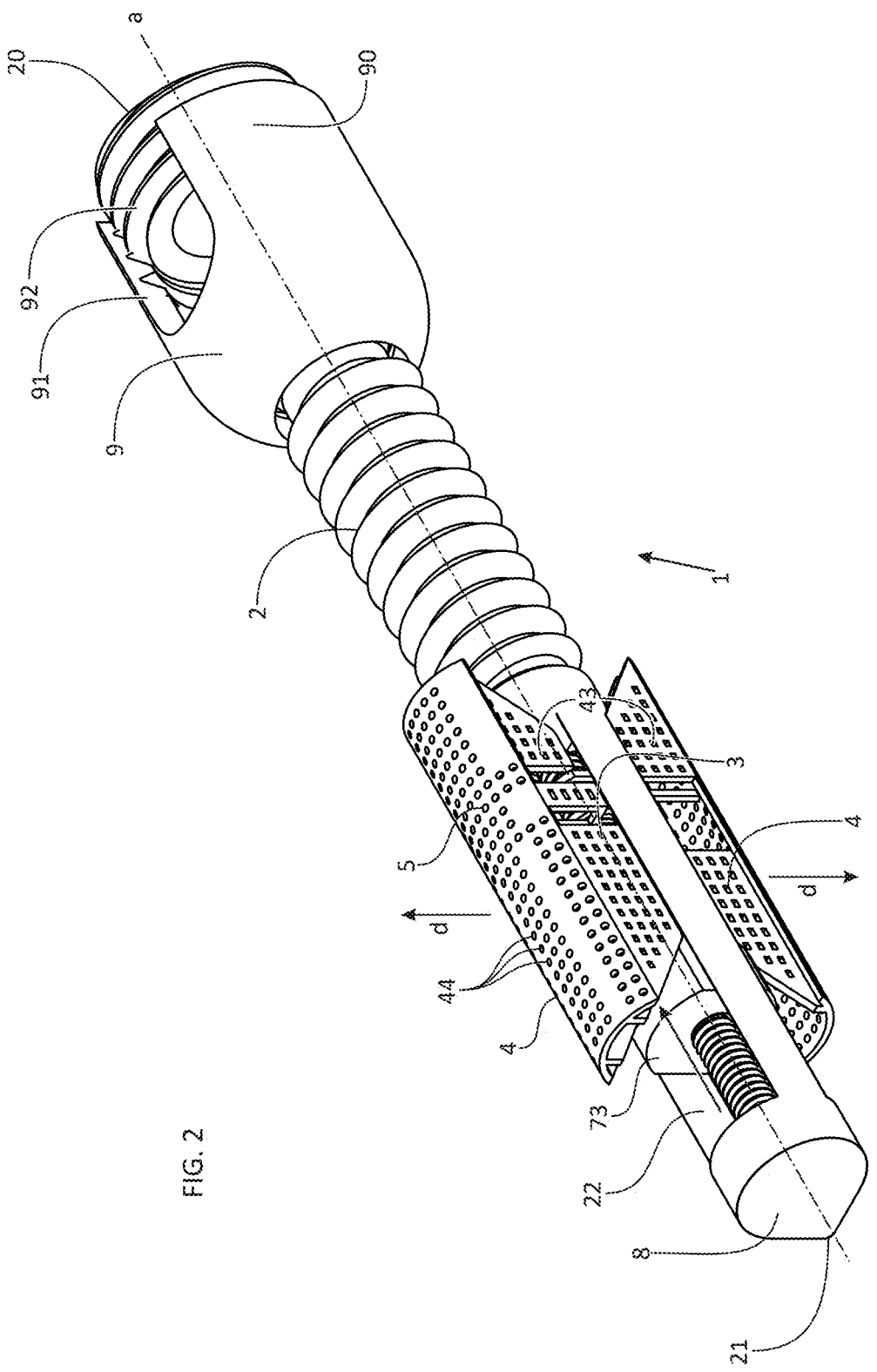
FIG. 2 schematically shows a perspective view of the example of FIG. 1 in an expanded state.
Figure 3:
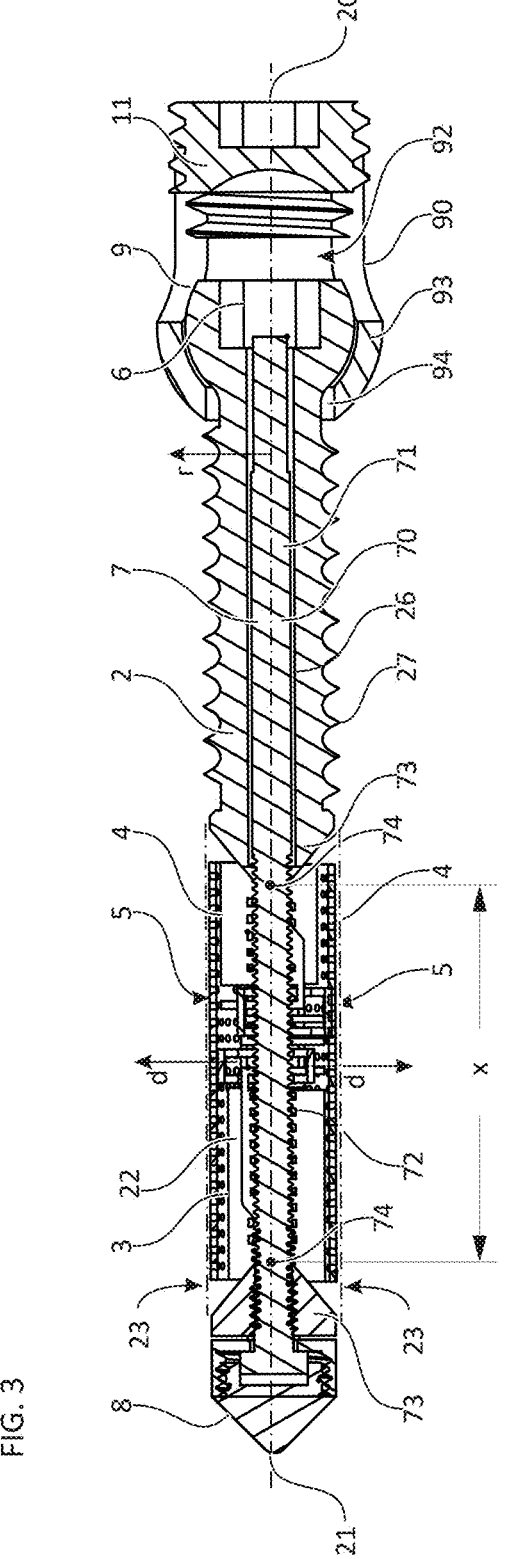
FIG. 3 schematically shows a cross-sectional side view of the example of FIG. 1 in the non-expanded state.
Figure 4:
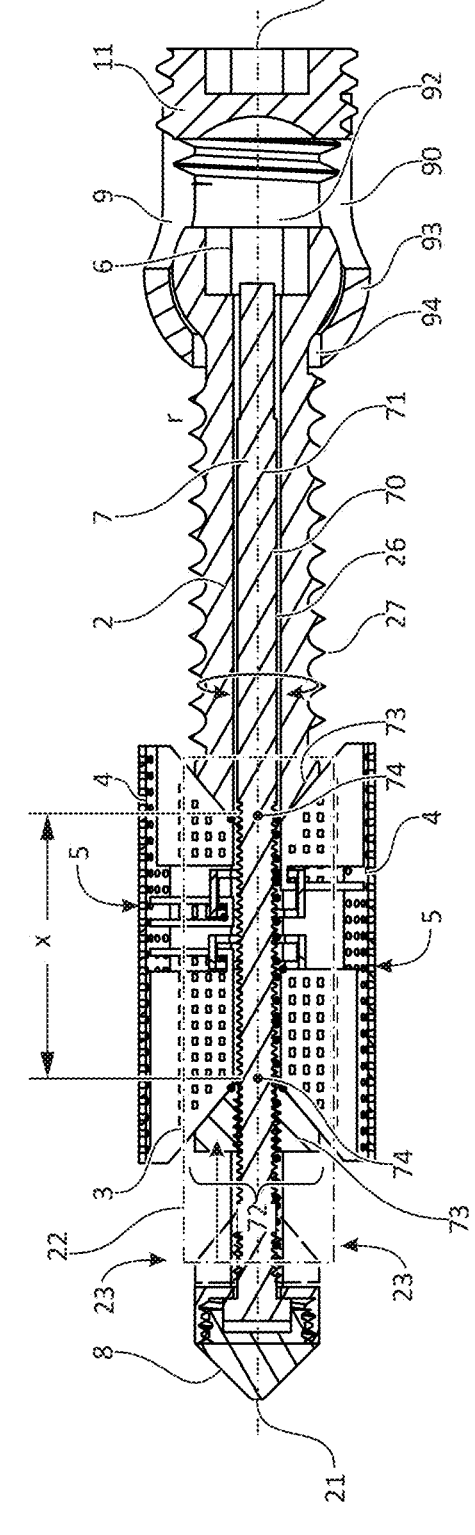
FIG. 4 schematically shows a cross-sectional side view of the example of FIG. 1 in the expanded state.
Figure 5:
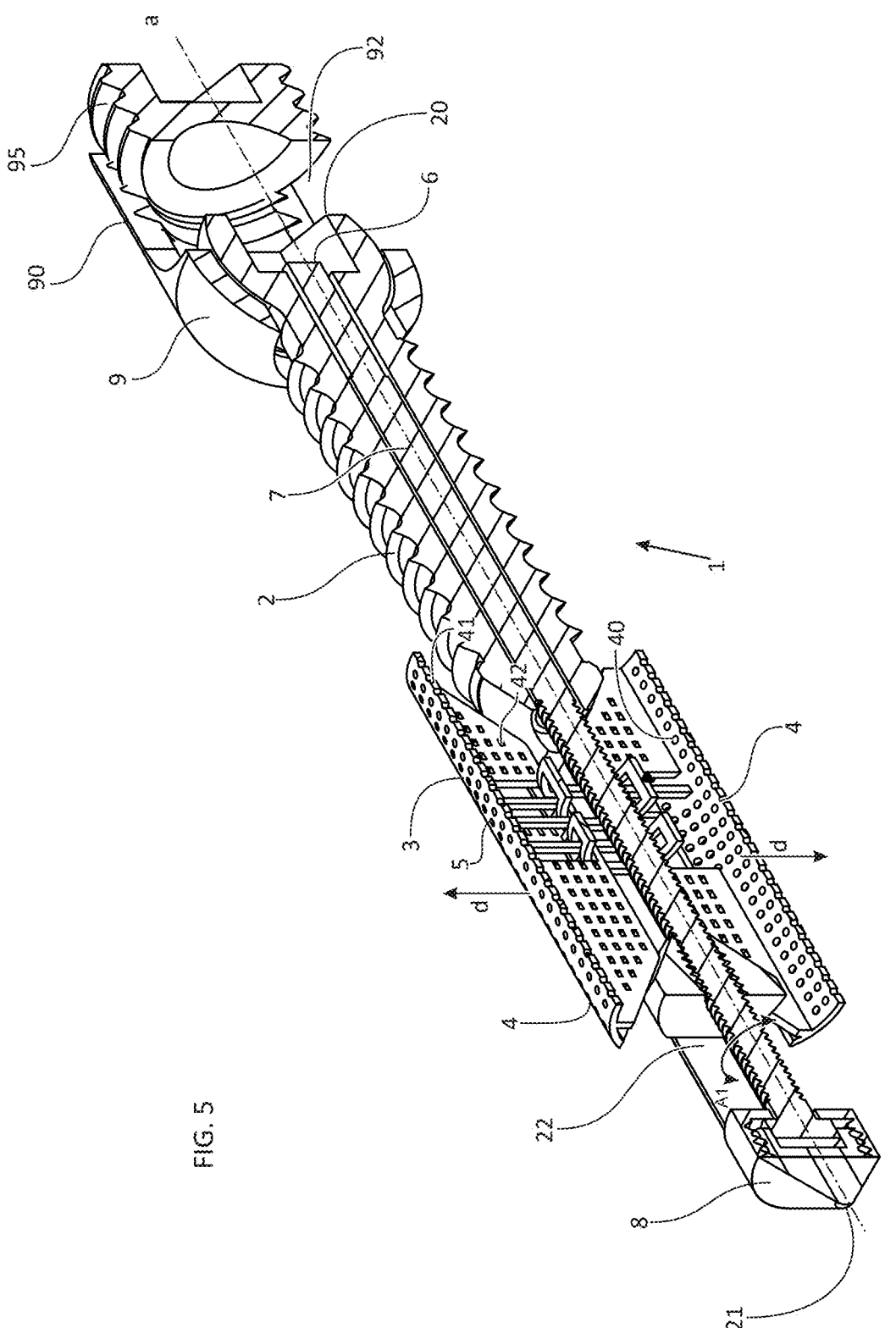
FIG. 5 schematically shows a perspective sectional view of the example of FIG. 1 in the expanded state.
Figures 6, 7:
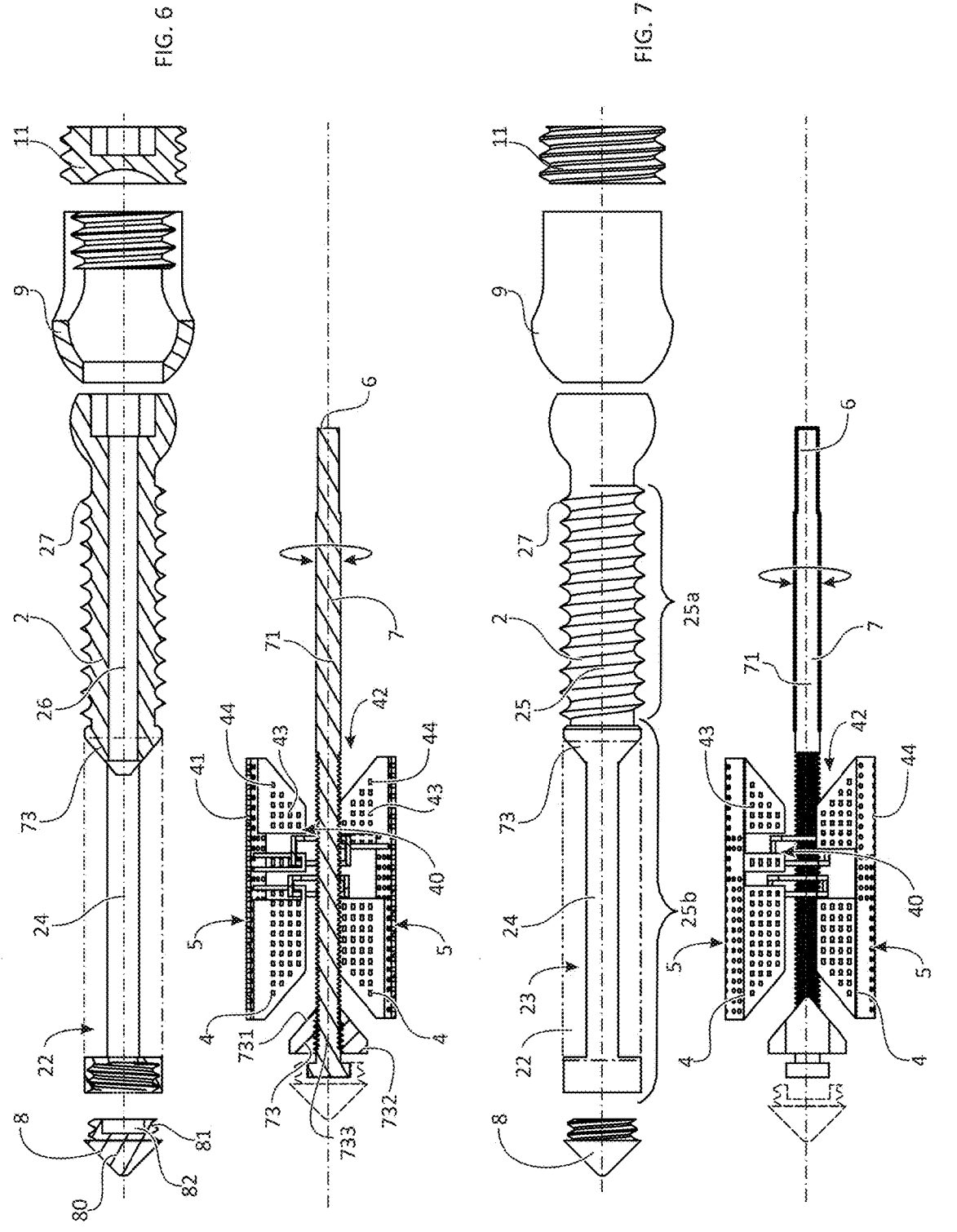
FIG. 6 schematically shows a sectional side view of an example of a kit of parts suitable to assemble the example of FIG. 1.
FIG. 7 schematically shows a side view of an example of a kit of parts suitable to assemble the example of FIG. 1.
Figures 8, 9:
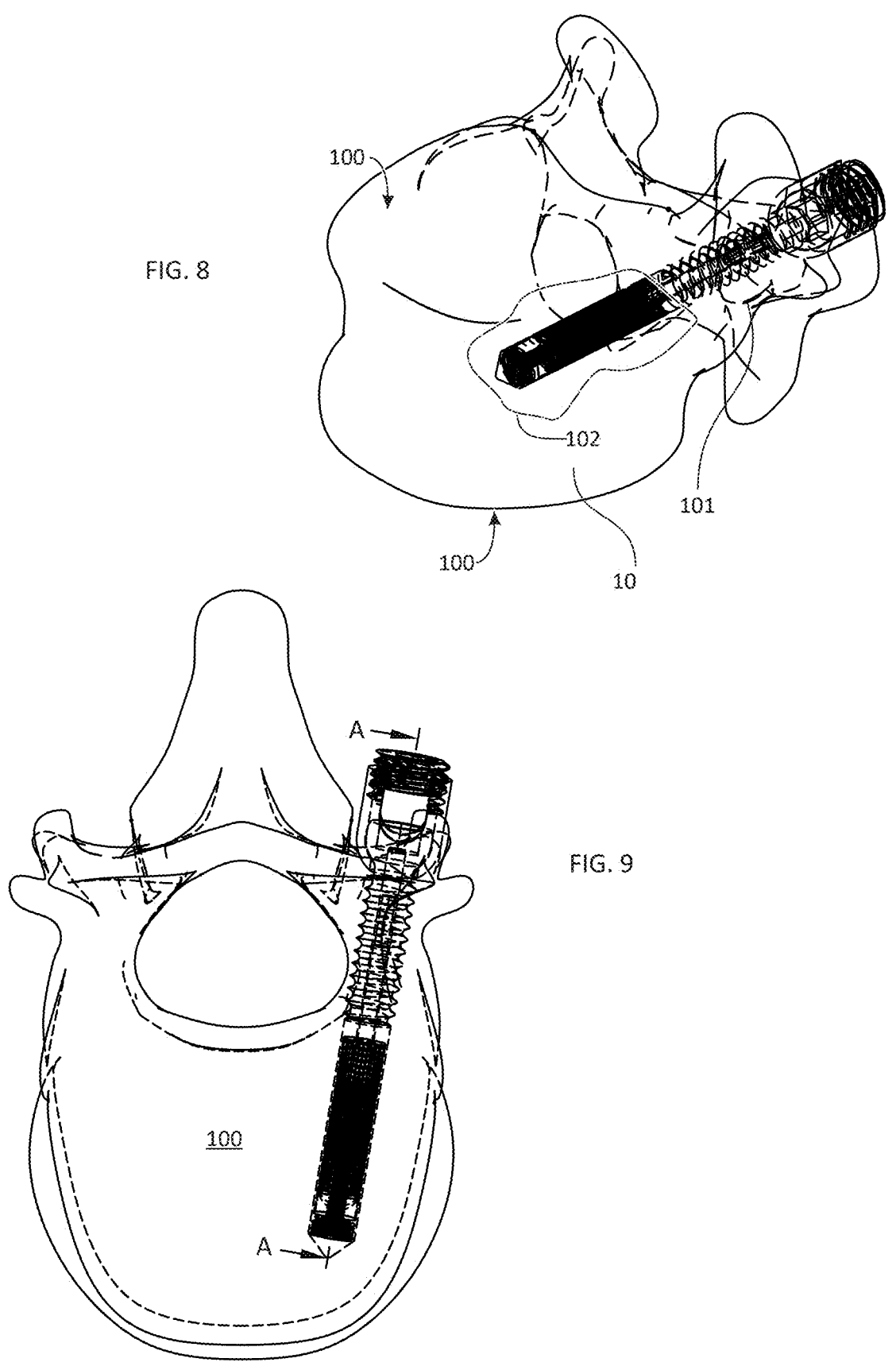
FIG. 8 schematically shows perspective view of a bone in which an example of an implant is anchored, with the implant in the non-expanded state.
FIG. 9 schematically shows a top view of the bone of FIG. 8.
Figures 10, 11:
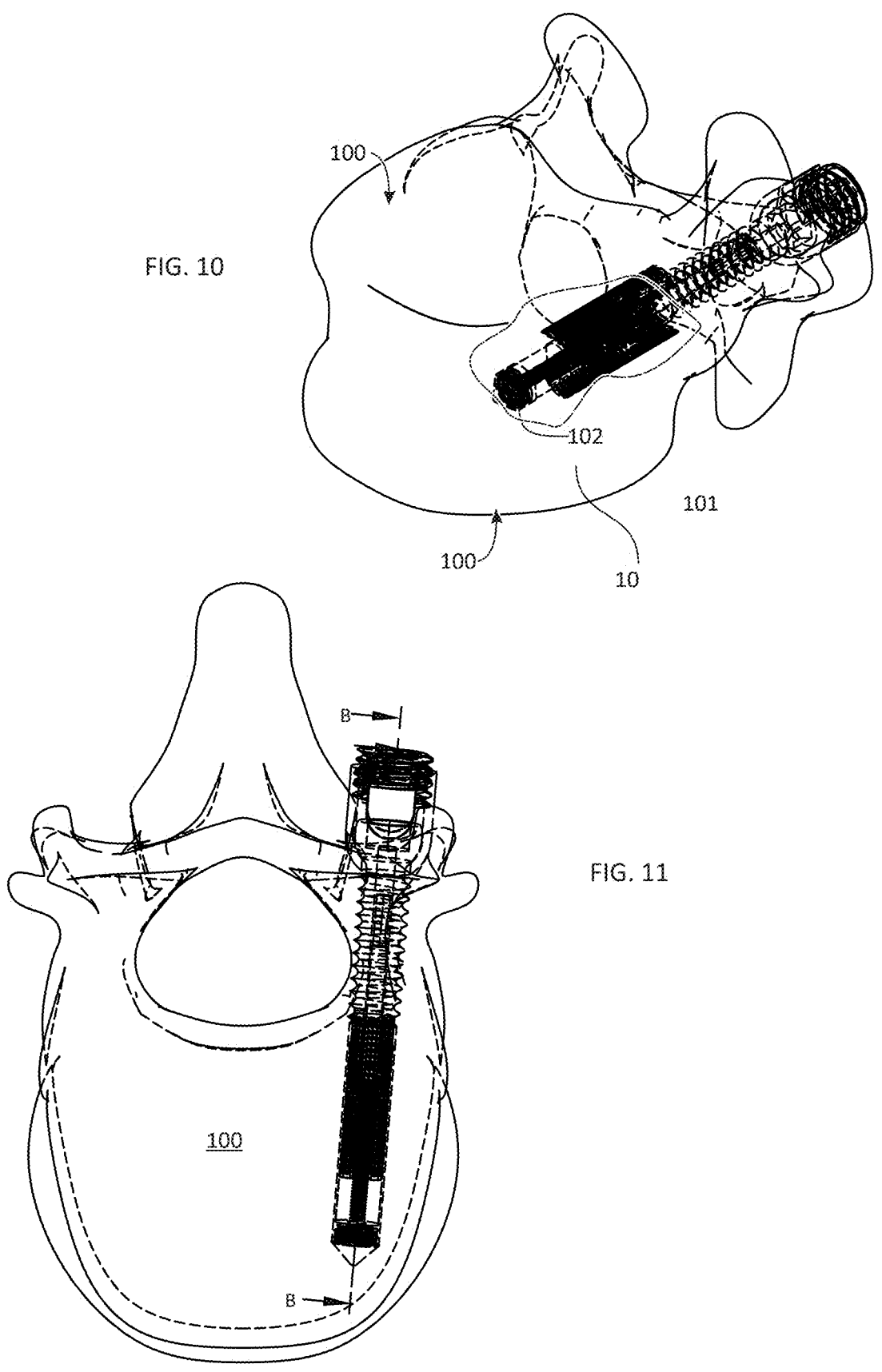
FIG. 10 schematically shows perspective view of a bone in which an example of an implant is anchored, with the implant in the expanded state.
FIG. 11 schematically shows a top view of the bone of FIG. 9.

As can be seen in FIGS. 3-5, a transmission 7 extends between the drive part and the expandable part 3. The transmission 7 engages on the load supporting surface 5 to transfer at least a part of the force exerted on the drive part, to move the drive part relative to the proximal end 20, e.g. torque, compressive or tensile force, to the load supporting surface 5. In doing this, the transmission 7 actuates a displacement of the load supporting surface 5 in the direction of expansion. More specifically, as indicated with the arrows A2 in FIG. 5, A3 in FIG. 2 and arrows d, the movement of the drive part 6 causes a series of movements of parts of the transmission 7 which is transferred to a movable piece 4 with the load supporting surface. In this example the movement is a displacement of the movable piece 4 along a path determined and controlled by the transmission 7. For instance, the transmission 7 can transfer the force exerted on the drive part into a force doing positive work in the direction of expansion d, which force acts on the movable piece 4. The transmission 7 can for example change the direction of the force, e.g. when the force on the drive part 6 is not in the direction of expansion and/or change the magnitude of the force exerted to a magnitude suitable to expand the implant against the loads acting thereon. In this example, the transmission 7 changes the movement of the drive part 6 into a push-out of the movable piece 4.

The implant 1 has a relative low risk of failure because the mechanical construction is relatively simple. The associated risk of movable parts being jammed during insertion or expansion is therefore reduced as well. More specifically, the expandable part 3 and the anchoring part 2 form together a mechanical system and not as in the prior art referred to in the section "Background of the invention" separate mechanical systems between which force cannot be transferred. To exert the expanding force, there is therefore no need to access the expandable part with an instrument that as in that prior art passes through one mechanical system, the pedicle fixation, to engage on different elements of another mechanical system to move those relative to each other. Instead, the drive part 6 can simply be moved relative to the anchoring part 2 to generate the thrusting force that expands the implant 1. The expanding force exerted on the drive part 6 is transferred to the expandable part 3, and the anchoring part 2 thereby, indirectly, exerts a force on the expandable part.

In addition, the ease of use is increased, because prior to exerting the expanding force the anchoring part can be anchored in the bone, and thus the bone itself can provide to a surgeon or other medical practitioner a point relative to which the surgeon can exert the force that drives the movement of the drive part 6. In the mentioned prior art, on the other hand, the implant is freely movable in rotation around, and in translation along, the main axis of the pedicle fixation and relative to the pedicle fixation. The fixation and the bone can therefore not used to exert that force and expand the implant itself. The surgeon therefore has to maintain the implant manually in position during expansion, and use separate parts of the implant to exert an expanding force between those.

The anchoring body 2 may be implemented in any manner suitable for the specific implementation. In the shown example, the anchoring body 2 is a monolithic body made in one piece, but alternatively it may be composed of several separate pieces which are e.g. screwed onto each other. As explained below in more detail, in a currently preferred example, the anchoring body is a monolithic, non-porous structure, but alternatively the anchoring body may have a porous outside and/or partially or completely porous inside.

The anchoring body 2 may have any suitable shape. The anchoring body 2, can, for example, have a smooth shape, i.e. the cross-section may be constant or vary, monotonically or not, (e.g. tapers) along the longitudinal direction, either locally or over the whole length without discontinuities or sharp edges. For example, the distal end 21 may be tapered whereas from the proximal end to the location of the expandable part 4 the cross-section may be constant. In this example, though the diameter is constant over the whole length.

The anchoring body 2 may be an elongate body, e.g. rounded or not rounded. In this example, the anchoring body 2 has for example rounded shape, more specifically a cylindrical shape, and although in this example this is a circular cylindrical shape, other cylindrical shapes such as elliptical cylinders may also be suitable, as well as other rounded shapes such as a cuboid (or other polyhedrons) with chamfered lateral edges, for instance. The anchoring body may, as in this example have a longitudinal axis a parallel to the longitudinal direction l, around which the drive part 6 may be rotatable relative to the anchoring body 2, for example, as indicated in the FIGs with the arrow.

The anchoring body 2 can be provided with a bore 26, such as a cannula, extending from the proximal end 20 towards the distal end 21. In such a case the transmission 7 can extend through the bore 26, and thus be embedded inside the anchoring body 2. This reduces the risk that e.g. during insertion in the bone the transmission 7 is damaged or gets stuck, such as due to bone fragments or chips getting stuck between the transmission 7 and the anchoring body. Although the bore 26 can be provided in differently shaped bodies, in this example the anchoring body 2 has a tubular shape, and the bore 26 has an open end at at least one and preferably both of the proximal end 20 and the distal end 21, through which the transmission 7 projects. The bore extends in this example from the proximal end up 20 up to the location of the expandable part 3.

The outside of the anchoring body 2 can have a friction enhancing profile for holding the implant 1 in the part of the bone 10, and more specifically which resists forces in the distal-proximal direction (that is from the distal end towards the proximal end and/or from the proximal end towards the distal end). The anchoring body 2 can for example have an outer surface 25 extending in the lateral direction, which may be unprofiled, partially profiled or completely profiled. The profile may for instance be ribbed, fluted and/or provided with helical threads. In this example, the outer surface 25 has a profiled area 25a where the outer surface is provided with a profile that extends circumferentially around the anchoring body 2 and extends in the lateral direction from the proximal end 20 up to an unprofiled area 25b, the unprofiled area 25b extending from the profiled area 25a up to the distal end 21. In this example, the expandable part 3 is located in the unprofiled areas 25b. Thus, the anchoring force is not exerted on the bone in the area of the expandable part 3, where the bone will typically be relatively weak and hence susceptible to further damage. Accordingly, despite being a single mechanical system still a spatial separation of the forces exerted on the bone can be obtained. The profiled area 25a serves to anchor the anchoring body 2 in the bone. When a force is exerted on the anchoring body 2 in the distal-proximal direction, the profiled area 25a transfers this force to the bone surrounding the profiled area 25a resulting in a counterforce being exerted by the bone in the opposite direction, and accordingly pulling or pushing of the implant 1 being resisted.

Figure 12:
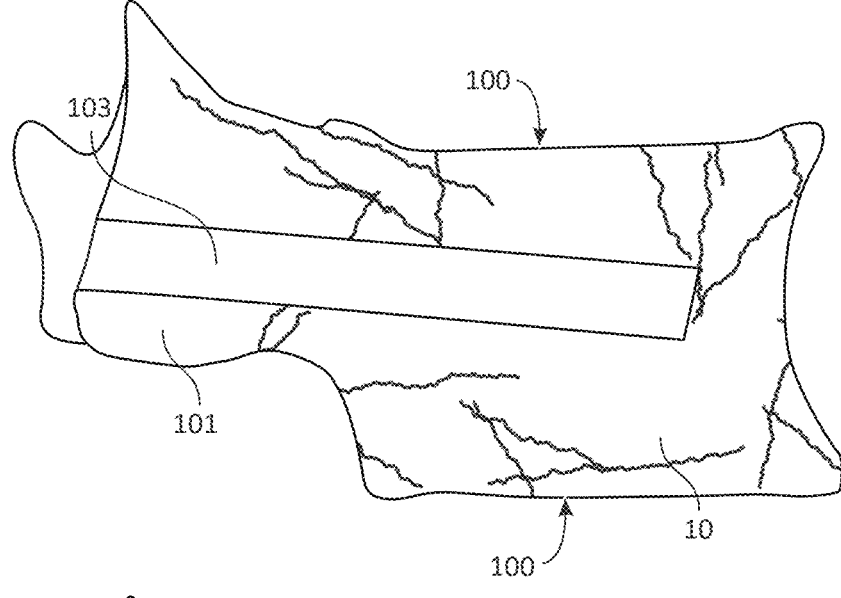
FIG. 12 schematically shows a cross-sectional view of the bone of FIG. 9 taken along a sagittal plane, prior to inserting the implant into the bone.
Figure 13:
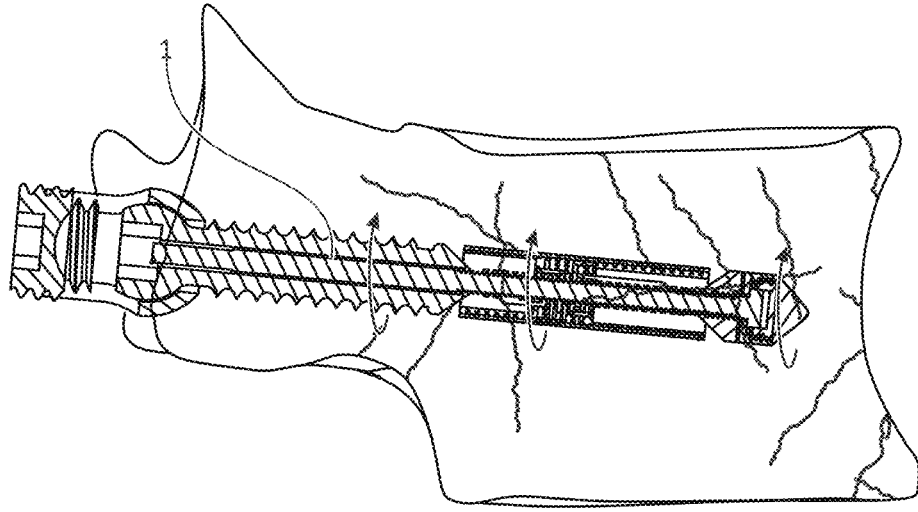
FIG. 13 schematically shows a cross-sectional view of the bone of FIG. 9 taken along a sagittal plane, after inserting the implant but prior to expanding the implant.
Figure 14:
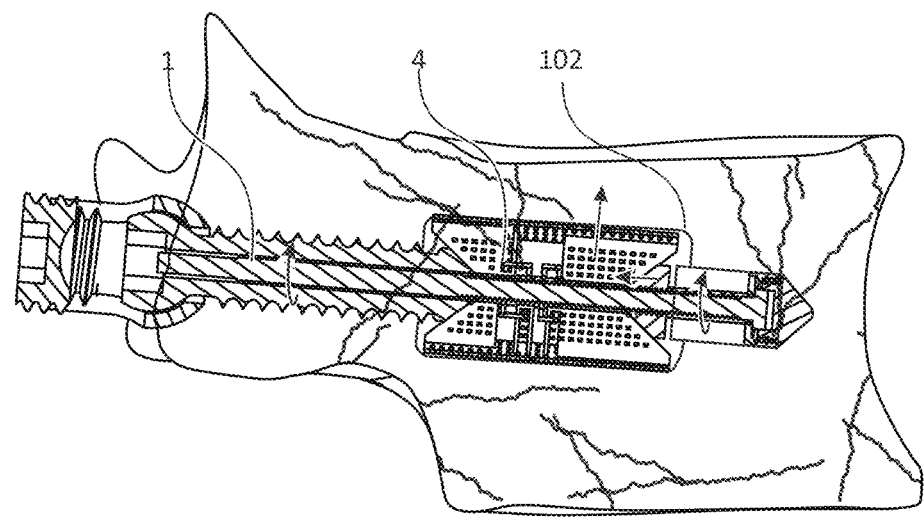
FIG. 14 schematically shows a cross-sectional view of the bone of FIG. 9 taken along a sagittal plane, with the implant expanded.

In this example, the outside 25 of the anchoring body has an elongate shape 2 which is provided (in the profiled area 25a) with ridges extending at an angle relative to the longitudinal direction. Although the ridges may e.g. all parallel (each ridge forming a closed loop), in this example the ridges are connected and form a helical thread 27. The tread 27 may be sufficiently sharp and rigid that upon rotational insertion in a pre-drilled cannula in the bone, the anchoring body forms a thread in the cannula, complementary to the thread 27 of the body, and the anchoring body 2 may thus be a thread forming screw body. In the shown example, this screw body is not self-tapping and accordingly is inserted in a pre-drilled cannula 103, as illustrated in FIG. 12-14. However, alternatively the anchoring body 2 may be self-tapping and e.g. at the distal end 21 be provided with a sharp point, and along the outside surface be provided with a self-tapping thread which extends from the point towards the proximal end 20.

Although the expandable part 4 may alternatively be located, seen in the direction from the proximal end to the distal end, beyond the distal end 21, in this example the expandable part 4 is located between the proximal end 20 and the distal end 21, and fixated relative to the anchoring body 2 as follows.

The part of the anchoring body 2 in which the expandable part 3 is located may, as in the example, be shaped as a slotted tube. More specifically, a space 22 in which the expandable part is located, is formed by a slot of the slotted tube. The slot has an opening 23 extending parallel to the longitudinal direction. In the initial, that is non-expanded position, the movable piece 4 is at least partly, in this example complete recessed in the slot. The load supporting surface 5 may then for example be flush with, or below, the outer surface of the anchoring body 2, as can best be seen in FIG. 3 but alternatively, the movable piece 4 may project (preferably slightly) beyond the outer surface. The movable piece 4 is movable through the opening 23 to the expanded position, as can be seen in FIG. 4.

The slotted tube has in this example two, opposite openings 23 facing each other, such that the anchoring body has a fork-shaped distal end 21 with prongs 24 extending in the longitudinal direction. As shown, the space 20 is formed between the prongs 24, and the expandable part 3 is located therein.

The prongs 24 are at one end thereof attached to each other by the anchoring body 2, and at the other end by a cap 8 which forms the tip of the implant and thus the distal end 21 in this example. The cap 8 may be implemented in any manner suitable for the specific implementation. The cap 8 may be cone-shaped, as in this example. The cap 8 and the prongs can be are a single piece, such integrally formed together or joint together after forming. Alternatively, as in this example, the cap 8 may be a separate piece fixated to the prongs 24. In this example, the prongs 24 are joined at the tip side end by an end part of the anchoring body on which the cap 8 can be mounted. As can be seen in FIGS. 3-5 and 6-7, the end part may for example be provided with a threaded bore in which the screw part 81 of a screw cap can be screwed. Alternatively, for example, the screw cap can be welded or otherwise jointed to the anchoring body 2. As more clearly shown in FIG. 6, for example, the screw cap 8 may comprise a hole 82, in this example a blind hole which closes of the distal end 21, and in which a terminating part of the transmission can be mounted. The screw cap 8 further comprises a cone-shaped part 80 which is oriented with the apex towards the distal end 21, thus forming a pointed tip of the implant.

Although in this example the expandable part 3 is thus located at the proximal side of the distal end 21 and in the anchoring body 2, alternatively the expandable part 3 may be located between the distal end 21 and the tip of the implant 1. In such a case for example, the prongs 24 may be implemented as an integral part of the cap and e.g. be screwed or otherwise attached to the anchoring body 2.

The expandable part 3 may be implemented in any manner suitable for the specific implementation. For example, the expandable implant disclosed in International patent application publication WO2005/120400, incorporated herein by reference, which has two movable pieces in the form of plates may be used. In such a case, e.g. the drive part 6 may extend through the bore 26, which in that document has reference number 80 and the opening, which is designated 39, of the expandable implant 1.

Also, the expandable part can for example be implemented as disclosed in Dutch patent application number 2022922, filed in the name of the applicant, and incorporated by reference.

In this example though, the expandable part 3 is implemented as disclosed in FIGS. 27-30 of the not published International patent application PCT/NL2020/050246 filed by the applicant, incorporated by reference as well. More specifically, in the shown examples the expandable part has, instead of a plate as in WO2005/120400, as movable piece at least one pre-shaped bulk block for filling up, in the expanded state, the cavity of the bone.

The movable piece 4 has a load supporting surface 5 for supporting a load acting on the bone, and a fixation interface for interfacing with a pre-shaped fixation which when interfacing holds the pre-shaped block in the expanded state of the bone support device in position, against the load, and inhibits the device from collapsing from the expanded state into the non-expanded state. Thus, to maintain the implant 1 in the expanded state no bone cement or other filling material is needed (although such may e.g. be used to attach the load supporting surface 5 to the wall of the cavity, hence as an adhesive material). In addition, when the expandable part is expanded, the movable piece with the load supporting surface ensure the structural integrity of the walls of the cavity. Hence, the implant may be used without cement filling the cavity space, which in the prior art is required to provide structural integrity to the walls of the cavity.

In the shown examples, the load supporting surface 5 is a non-planar surface, which is curved in the circumferential direction of the anchoring body and flat in the longitudinal direction. Alternatively, the load supporting surface 5 may have another dome-shaped curvature, like a cap (such as an ellipsoid cap) and for example be curved in two directions, e.g. in the longitudinal direction as well as the circumferential, or be partially flat, for example have chamfered edges or be provided with a flange, or be completely flat, just to name a couple of examples.

In the shown example, the expandable part 3 is expandable by displacing the movable piece 4, relative to the anchoring body 2, in the direction of expansion d. In this example, the displacement of the movable piece 4 is a rectalinear displacement. As explained in more detail with reference to FIGS. 8-13, upon expansion of the implant 1, the load bearing surface 5 is displaced outwards with the displacement of the movable piece 4, in the direction of expansion, until the load bearing surface 5 abuts to the wall of the cavity. During this, the movable piece 4 itself is only displaced and does not expand or deform, although under the counterpressure of the bone material some flexing may occur. That is, the movable piece 4 is pre-shaped and retains its shape during expansion of the implant. For the purpose of expansion, the movable piece 4 can thus be regarded as a rigid body.

In this example, the movable piece 4 has an inward facing side 40, facing away from, and preferably opposite to the load supporting surface 5 on which the transmission engages. The moving parts thereof are therefore shielded by the movable piece 4, which reduces e.g. failure caused by bone fragments or chips getting stuck.

The movable piece 4 may be displaced to come, at some point during the expansion, to contact the bone. In practice, the implant 1 is expanded until the load bearing surface 5 deforms the wall of the cavity 102, and e.g. pushes the bone material forming the wall outwards, in the direction of expansion, to at least partially or completely restore the outer shape of the bone 10. In the shown example the movable piece 4 will not bend, but alternatively the piece may flex under the counter pressure exerted by the bone, e.g. by the wall of the cavity 102. The load supporting surface 5 may, as a consequence, bend under the exerted force.

In the shown examples, the expandable part 3 has two movable pieces 4. However, the expandable part may comprise one, two or more movable pieces 4. In case there are multiple movable pieces, they can differ in direction of expansion, and the load supporting surfaces 5 of the pieces be oriented parallel to each other, perpendicular, or at oblique, acute or obtuse angles relative to each other, and the directions of expansion be opposite, perpendicular or at acute or obtuse angles. In the shown example, for instance, the two pieces 4 are be movable in opposite directions and the load supporting surface 5 thereof are facing away from each other, such that the implant 1 can expand in opposite directions.

In this example the expandable part 3 expands such that after expansion the load supporting surface 5 is discontinuous with the outside of the anchoring body 2. Said differently, after expansion, the load supporting surface 5 projects at a lateral side of the implant 1 outwards in a direction perpendicular to the longitudinal direction, and the lateral side of the implant 1 exhibits a stepped profile, with at least one step located at a transverse edge of the load supporting surface, and a gap between this edge and the outside of the anchoring body. In circumferential transverse direction of the implant, the load supporting surface 5 is likewise discontinuous with the outside of the anchoring body 2. That is, the expandable part 3 does not expand over the entire circumference, but only over, in transversal direction, the spaced apart parts where the movable pieces 4 are displaced to project in the transverse direction. In circumferential transverse direction, there is thus a gap between the lateral edges of the respective load supporting surfaces in the expanded state. As can e.g. be seen in FIG. 2, in which the prongs 24 of the anchoring body 2 extend in the circumferential direction between these lateral edges. In this example, the expansion is in the transverse direction l-shaped but alternatively, for example the expandable part may be implemented to exhibit an L-shaped, X-shaped or +shaped expansion.

In the shown examples, the anchoring body 2 has a longitudinal axis a extending from the proximal end 20 towards the distal end 21, and the anchoring body is rotationally movable around the longitudinal axis relative to the bone 10 to anchor the implant 1, and to orient the load supporting surface 5, as illustrated e.g. in FIG. 13. The expandable part 3 will, while in the non-expanded state, remain in position relative to the anchoring body 2 when the anchoring body 2 rotates with the anchoring body 2, and more specifically is fixated thereto in the direction of rotation. In addition, in this example, the expandable part 3 does not displace in the longitudinal, or other directions, relative to the anchoring body 2 in the non-expanded state. By suitable rotation of the anchoring body 2, the expandable part can thus be positioned and oriented in the intra-osseous cavity as desired by a medical practitioner.

On the other hand, to expand the implant after anchoring, the movable piece 4 is movable outwards from the anchoring body 2, in a radial direction perpendicular to the longitudinal axis. This allows to implant the implant in the bone in separate phases, and more specifically to first anchor the implant, and only thereafter bring the implant into its expanded state. This separation in turn allows a medical practitioner to precisely position the implant and expand it up to desired amount of expansion.

As illustrated in FIGS. 1-5, the movable piece 4 is movable along a predefined path. The path can e.g. be a straight path perpendicular to the longitudinal direction. As can be seen in FIGS. 3 and 4, during the expansion, the movable piece 4 may move in other directions as well, and here, when expanding, the movable piece 4 is displaced in the longitudinal direction towards the proximal end as well as in the direction of expansion, as can best be seen in FIGS. 3 and 4.

In this example in the non-expanded state the load supporting surface 5 is flush with, and in the prolongation of, the outer surface, as can be seen in FIG. 3. In the expanded state, the load supporting surface 5 projects radially outwards from the outer surface 25 and partially overlaps in the longitudinal direction with the outer surface 25 of the anchoring body 2.

Although other trajectories are possible, in the shown example the movable pieces 4 displace rectilinearly, here in a direction at an oblique angle to the longitudinal direction. Said differently, during expansion, the movable pieced 4 are slightly retracted in the longitudinal direction, towards the proximal end 20. This allows to release a part of the tensile stress induced on the bone by the anchoring body 2.

The movable piece 4 may be implemented in any manner suitable for the specific implementation. The movable piece 4 may for example be implemented as a plate oriented perpendicular to the direction of expansion, with an outward facing side with the load supporting surface 5 and an inwars facing side facing towards the inside of the implant 1. For example, the plate may be implemented as in the expandable implant disclosed in International patent application publication WO2005/120400.

In this example though, the expandable part 3 comprises as movable pieces 4 bulk blocks such as disclosed in aforementioned PCT/NL2020/050246. The expandable part comprises at least two movable pieces but any other number may be suitable. Each block is movable, from an initial position, away from each other to expand the device. In this example, the movable pieces 4 form an inter-block space between the bulk blocks, or at least increase the spacing between the load supporting surfaces 5 upon expansion of the device. As can be seen in e.g. FIG. 2, in the expanded state the space between the load supporting surfaces 5 is, at least partially or completely filled by the bulk blocks 4. More specifically, for each movable piece 4 the space between the location of the load supporting surface 5 in the non-expanded state and the location of the load supporting surface 5 in the expanded state is at least partially, and in this example completely, filled by the bulk block.

The bulk block may be closed, and e.g. be massive or hollow, structures. Alternatively, as in this example, the bulk block may have an open structure, with the material of the block filling less than 100% of the volume of the block, and the inside of the block being accessible from the outside. The open structure, as is explained below in more detail, allows bodily tissue and fluids to enter and/or grow in the bulk blocks after implantation. Accordingly, the implant can integrate into the bone structure and the open bulk block forms a bone scaffold.

The inside 42 of the movable piece 4 may have an openness, i.e. the aggregate volume of the inside 42 occupied by the structure relative to the total volume of the inside 42 of at least, or equal to one of the group consisting of: 70%, 80%, 90%, such as less than one of the group consisting of: 95%, 85%, 75%. The member may have an openness which (of course) is more than 0%, such as at least 10%, such as at least 20%, such as at least 30%, such as at least 40%, for example at least 50%, such as at least 55%. Currently most preferred is an openness in the range of 50% to 80%.

The open structure allows the implant 1 to incorporate in the bone 10, i.e. ingrowth of bone 10 matter inside the implant 1 can be obtained in addition to bone on-growth on the load supporting surface 5, and/or if present other interfaces between the implant 1 and the bone 10. More specifically, the solid parts of the structure provide a seed surface for bone material, and, after implantation, form a substrate on which osteoblasts and stem cells can grow. Without wishing to be bound to theory, it is currently believed that the solid parts initially form a seed layer for a cell growth substrate. The cell growth substrate can for example be formed by substances adsorbed to the surface of the solid parts, like proteins, water molecules and/or lipids. Also, the substrate may comprise substances attached to the solid parts of the bulk block, like blood platelets. After formation of the growth substrate, the bone 10 may grow. For example, in case of osseo-integration, osteoblasts or their progenitors, such as osteochondro-progenitor cells or mesenchymal stem cells, will grow thereon and subsequently form the bone 10 matrix in the pores, thus creating an intimate bond between the bone 10 and the implant 1.

In case of closed structures, the bulk blocks may e.g. abut with the inwards facing sides 40 in the non-expanded state. The volume that lies between the load supporting surfaces 5 can then be increased by expanding the implant, because the load supporting surfaces 5 will lie further away from each other. In the shown example though, in the non-expanded state, the inwards facing sides 40 of the bulk blocks extend through each other, and the blocks are movable to increase the distance between the load supporting surfaces 5, and to take the mutually interdigitated parts out of each other. Thereby, the ratio of expansion can be high because the overall volume in the non-expanded state is low. For example, the overall volume can be less than the total volume of the separate individual bulk blocks, and preferably is as close to the volume of the largest separate individual bulk block as possible.

When expanding, the interdigitated parts may remain partially interdigitated, such that the inwards facing sides 40 are oriented facing away from each other. Alternatively, as in the examples, the interdigitated parts may be moved completely out of each other, such that the inwards facing sides 40 are spaced apart and face each other. This allows to further increase the ratio of expansion, which in the examples is about 3, that is the distance between the load supporting surfaces 5 can be increased to maximally a factor of about 3, relative to the non-expanded state.

As best seen in FIG. 5, in this example each movable piece 4 has at the inwards facing side 40 a number of projections which project inwards, i.e. in this example towards the other piece 4. In the non-expanded state, at least some of those projections abut in this example to the inwards facing side 40 of the other block. The projections define the volume that the movable piece fills up in the expanded state and divide the volume in a number n of spaces, n being a positive integer of at least 2. Depending on the type of treatment, in the spaces for example a bone graft can provided which allows bone to grow in this space.

The spaces are open at the side facing the other block, i.e. the inwards facing side 40 and closed at the opposite, outwards facing side, and in at least some or all of the spaces a complementary projection of the other block can be admitted to interdigitate the blocks. At the other sides they may be fully enclosed by the projections, or open at one, two, three side (e.g. in the case of panel-shaped projections) or all sides (e.g. in the case of pillar-shaped projections). In this example, the projections are shaped as panels 43. The panels 43 provide an open structure to the blocks that at the same time is strong and rigid and capable of resisting and transferring the loads acting on the load supporting surfaces after implantation. However, the blocks may additionally or alternatively have other projections which can be interdigitated. For example, a block may be provided with pillar shaped projections which can be admitted in tubular projections of the other block, for example. Or both blocks may be provided with pillars and the pillars of one block be offset relative to the pillars of the other block, such that the pillars of the one block can be admitted in the spacing between the pillars of the other block.

The panels 43 enclose a respective space at least at two sides. In this example, two parallel sides are closed by the panels, while the space is open at the lateral ends of the panels. The panels 43 extend in this example parallel to each other, in the longitudinal direction but other orientations may be suitable as well. As shown, the space between the projections is also open in the direction of expansion. The projections are positioned such that in the non-expanded state the projections of the other movable piece extend in that space and the projections are thus interdigitated. The spacing between the panels is relatively small though, such that the space has a slotted shape with a width which in this example larger than the thickness of the panel of the other block that is to be admitted in the slot-shaped space, and preferably twice or more of the thickness. This reduces the risk that the interdigitated blocks get stuck during expansion.

In this example, the panels are provided with through pores 44 and the inside 42 of the movable piece 4 is thus porous, with the spaces being in communication through the pores when the implant 1 is expanded. This accelerates the propagation of bone in-growth and on-growth in the inside 42. As shown, in these examples, the movable pieces 4 may have at at least a part of their load supporting surface 5 open or outer pores as well. The open inside 42 can be in communication via the outer pores with the bone, which allows bone ingrowth into the inside 42.

The load supporting surface 5 is defined by an outward facing side of the movable piece 4. The movable piece 4 may have, as in this example, an exposed porous layer 41 forming the load supporting surface 5, which is provided with outer pores 44, here over the complete load supporting surface 5. The outward facing side may be closed, with only a porous top layer (or be completely non-porous) and the movable piece thus be closed at that side. However, in this example the movable pieces 4 are open at all sides, and the outward facing side is in this example completely porous. The load supporting surface 5 and the inwards facing side 30 are thus in communication, and in this example, the open inside and outer pores form an integral network for osseointegration of the expandable part in the bone.

The porous load supporting surface 5 may for example have an openness of at least 5%, for example at least 10%, and preferably at least 50%, such as at least 80%. The openness will of course be less than 100%, and may e.g. be 90% or less, for example less than 70%. The openness is defined as the ratio of the aggregate non-closed areas of the outer pores occupied at the outer surface and the total area of the outer surface.

Each of the inside 42 of the movable piece 4, the projections 43 and the load supporting surface 5 may have a porosity of at least, or equal to, one of the group consisting of: 70%, 80%, 90% and less than 100%, such as less than one of the group consisting of: 95%, 85%, 75%. The member may have a porosity which (of course) is more than 0%, such as at least 10%, such as at least 20%, such as at least 30%, such as at least 40%, for example at least 50%, such as at least 55%. Currently most preferred is a porosity in the range of 30% to 80%. Although not limited thereto, currently preferred is an average size of the pores between 0.1 and 3 mm, with more preference between 0.25 mm and 1 mm, such as in the range of 0.4 mm to 0.9 mm. Depending on the specifically implementation, the pores may all have the same size, or have or varying sizes (e.g. when the sizes are distributed according to a Gaussian or a normal distribution). For example, at least 90% of the number cells can have a size between 0.1 and 3 mm, or between 0.2 mm and 1.5 mm, such as between 0.2 mm to 0.9 mm. The pores in can be of any suitable type, and for example comprise or consist of open cells. The structure can for example be an open cell structure, such as made of a biocompatible metal. The open cell structure can be homogenous with pores of same shape and/or dimension or heterogenous with pores differing in shape and/or dimensions.

The combined movable pieces 4 may e.g. have complementary shapes. More specifically, when the movable pieces are correctly placed onto each other and the insides of the movable pieces 3,4 are positioned interdigitated into each other, they form, in this example together with the part of the anchoring body extending in the lateral direction besides the movable pieces, e.g. a cylindrical or other shape of which in circumferential direction the outside surface is smooth, i.e. without sharp edges. To that end, the outwards facing side of the piece 4 is curved in the circumferential, transverse direction of the anchoring body 2, such that in the non-expanded state this is continuous with the curvature of the prongs, i.e. when the lateral edges of the side 45 abut to the corresponding edge of the prong 24, they form a smooth body, in this example with a rounded shape, as is best seen in FIG. 1.

The drive part 6 may be implemented in any manner suitable for the specific implementation. In this example, the drive part 6 is located at the proximal end 20 of the anchoring body 2, and projects out of the anchoring body 2. Alternatively, the drive part 6 may e.g. be recessed in the bore 26 and e.g. be shaped to mate with a deep socket wrench. In the shown example, the drive part 6 is a rotary drive head on which a mating tool (not shown, such as an unmotorized or motorized tool, e.g. a hex or other wrench) can engage to exert torque and rotate the drive head relative to the anchoring body 2 around the longitudinal axis a. In this example, the drive part 6 is shaped as an external drive head on which a female tool can be placed to engage with the drive head, such as a square, hexagonal, pentagonal or external torx, but alternatively the drive part 6 can be shaped as an internal drive head, such a hexolobular socket or a torx socket, or as a clutch or a thumbscrew for example in which a male tool can be placed to engage with the drive head. In this example, the drive part 6 is a drive head of an axle, also referred to as a spindle, which extends through the bore 26 in the anchoring part 2, and which is an implementation of a driving part 70. The spindle is rotatable around its axis, but is secured in all other directions relative to the anchoring part 2. By mating the tool with the drive part 6 and exerting the torque with the tool, the spindle will be rotated around its axis relative to the anchoring part 2, as indicated with arrows A1 and A2 in FIG. 5, and thereby the mechanical actuator 72 located below the movable piece 4 be driven. Alternatively, the drive part 6 may be e.g. implemented as a manually driven rotary head, e.g. a knob or handle which the medical practitioner can rotate manually without using a tool. Also, in case the transmission is not of a rotary type, for example the drive part 6 can e.g. be a pulling or pushing drive, such as the end of a cable which can be used to tension the transmission 7 to expand on the expandable part 3. In such a case e.g. the bore 26 can be implemented as a cable housing for a Bowden cable. Alternatively, for example the drive part 6 can be a hydraulic or pneumatic drive head in case of a hydraulic or pneumatic transmission, for instance.

The transmission 7 may be implemented in any manner suitable for the specific implementation. For example, the transmission may comprise a system with articulated arms that engage with respective ends on the movable piece and of which other ends can be moved, such as as in WO200512040 e.g. by pulling a cable to rotate the arms and push the movable piece outwards. In the shown example, the transmission 7 comprises a mechanical actuator 72 located below the movable piece 4, which engages with the inward facing side, and a driving part 70 extending through the bore 26 arranged to drive the mechanical actuator 72. The shown example is a self-locking transmission 7, and accordingly if the driving force is removed, the movable pieces 4 will remain in position and the expanded implant will not collapse (unless of course a maximum load threshold is exceeded and the implant breaks down). This obviates the need to fill the cavity with bone cement, although some bone cement may be used to join the load supporting surface to the wall of the cavity.

Although the driving part 70 may generally be any suitable driving part, such as a cable or a hydraulic of pneumatic cylinder, in this example the transmission 7 comprises as a driving part 70 a rod 71, which can be moved relative to the bore 26. The rod 71 may be e.g. rotatable relative to, and in, the bore 26 around a longitudinal axis a parallel to the longitudinal direction l but not translationally movable in the longitudinal direction relative to the bore 26, and be implemented as the spindle mentioned above or other.

In the shown example, for example, the distal end of the rod 71 is secured in the distal end 21 of the anchoring body 2. As shown, the rod 71 extends through a hole in the anchoring body 2 at the distal end 21 and has a knob with a larger diameter than the hole, such that the knob cannot move towards the proximal end 20 beyond the hole. The hole and the part of the rod 71 in the hole are both unthreaded and the rod 71 can freely rotate in the hole without causing a translational movement. In the opposite direction, the knob is locked by a cap which is mounted, in this example screwed, onto the distal end 20. This in addition facilitates a simple assembly of the implant 1 by inserting the rod 76 from the distal end 21 into the hole and thereafter mounting the cap 8. However, it will be apparent that the rod may be secured in any another suitable manner, and that instead of a knob at the end, e.g. an intermediate part of the rod may have a radial projection which is admitted in a groove in the bore 26, for example or which is locked between the distal end side opening of the bore 26 and a cap mounted on the opening, for instance.

As further shown, the rod 76 extends through the bore 26 between the expandable part 3 and the proximal end 20 and is secured in the radial direction r by the bore 26. The proximal end of the rod 76 is provided with the drive part 6, as explained before, and in this example projects out of the bore 26 at the proximal end 20 of the anchoring body 2.

As explained below in more detail, the mechanical actuator 72 is located between the bore 26 and the distal end 21, in a threaded part of the rod 76 which lies in the space 22. The mechanical actuator 72 is coupled to the rod 76 and engages with the thread, such that the rotation of the rod 76 causes a translational displacement of the movable pieces 4, and more specific a pushing by the mechanical actuator 72 at the inwards facing side 40 of the movable pieces 4.

The mechanical actuator 72 may be implemented in any suitable manner. In this example the mechanical actuator comprises at least two actuating elements 73 mounted on the driving part 70 at positions spaced apart in the longitudinal direction. In this example, one actuating element is a separate element, separate from the anchoring body 2 and movable relative thereto as indicated with the arrow in FIGS. 2 and 4, whereas the other element is formed by the anchoring body 2 and more specifically by the distal end side opening of the bore 26.

Said differently, at the proximal end side, but this may also or additionally be the distal end side, of the space 20 the anchoring body 2 forms a respective actuating element 73 of which the position is stationary relative to the anchoring body 2, whereas other actuating elements 73 are formed by a separate piece located in the space 20 and which are movable in the space 20 in the longitudinal direction relative to the anchoring body 2. The mounting positions are likewise respectively stationary and movable in the longitudinal direction relative to the proximal end 20. The mechanical actuator 72 in this example thus operates by moving the separate element 73 towards or away from a part anchoring body 2 at an opposite side of the movable pieces 4, which causes the movable pieces to be pushed outwards. In this example, the movement of the separate element is along a predefined path, guided and defined by the rod 71. The actuating elements push from both sides, seen in the longitudinal direction, on the movable pieces. Accordingly, in this example by moving the separate actuating element towards the anchoring body 2, in the longitudinal direction, both the separate actuating element 73 and the anchoring body 2 push on the inwards facing side of the movable piece in the direction of expansion, causing the displacement of the movable piece in that direction.

The actuating elements 73, and therefore the mounting positions are movable towards to each other in the longitudinal direction by a motion of the driving part 70. In this example, the movement is caused by the rod 71 but it will be apparent that e.g. actuating elements 73 may be moved by e.g. pulling a rod or cable at the proximal end 20 to e.g. pull one actuating element relative to the other or in another suitable manner. When the positions are moved, the actuating elements 73 push the movable piece 4 in the direction of expansion.

The actuating elements 73 can e.g. form a mechanical linkage between the driving part 70 and the movable piece 4, and for example the expandable part be implemented as the expandable implant 1 disclosed in International patent application publication WO2005/120400, which is incorporated herein by reference. In such a case, the force applied to bring the ends designated 20 and 21 in this publication together may be exerted by the driving part 70, for example by mounting them on the rod 71.

In this example though, the actuating elements 73 are blocks with can be moved relative to each other, as illustrated with the arrow in FIGS. 2 and 4, to push the inwards facing side 40 of the movable pieces outwards, in the direction of expansion. To that end, the actuating elements 73 have an inclined plane 730, inclined relative to the longitudinal direction l of the anchoring body 2. The inclined plane 730 contacts the inwards facing side 40 and is oriented to slide over the inwards facing side 40 to push the movable piece 4 when the actuating elements 73 are moved towards each other. The actuating elements 73 thus act like wedges in this respect.

Although other shapes may be suitable, in this example the actuating elements 73 have a conical shape and are oriented with their axial direction extending in the longitudinal direction, and the bases 731 of the conical shapes facing away from each other. Thereby, a single actuating element 73 can move several movable pieces contacting the element 73 at different locations, at the same time, which makes the actuator mechanically less complex. Thus, by reducing the distance between the actuating elements 73, the movable piece(s) 4 contacting the actuating element 73 is pushed outwards and the expandable part expands.

Although the distance can be changed in any suitable manner, in the shown example, the rod 71 extends in a passage 732 through the actuating elements 73, i.e. through the anchoring body 2 and the separate actuating element 73, and engages with at least one of the actuating elements 73 to transform a motion of the rod 71 in a movement of the engagement positions. More specifically, the rod 71 is threaded over a trajectory of the separate actuating element 73 and the rod 71 extends through the actuating element 73 to rectalinearly move the actuation element 73 by engagement with a thread in that actuating element 73. The rod 71 and the actuating elements 73 thus form a moving nut-spindle system of which the rod 71 forms a spindle and the actuating element 73 engaging with rod 71 forms a moving nut, which may be movable along the rod 71 in the longitudinal direction, relative to the distal end 21.

In this, the anchoring body 2 inhibits rotating of the separate actuating elements 73 around a rotational axis parallel to the longitudinal direction and thus ensures that the separate actuating element only moves linearly, parallel to the longitudinal direction. Thus, the risk of the actuating elements getting stuck is reduced as well. To that end, the actuating elements 73 are located between the prongs 24 and inhibited by the prongs 24 from rotating over more than a predetermined angular range. The prongs 24 have an actuating element facing side which is less curved in a radial direction around the longitudinal direction than a circular cylinder, and the actuating element 73 located between the prongs 24 has a complementary contact surface which abuts to the actuating element 73 facing side, and are slideably engaged with the prongs 24.

As shown, the implant 1 may be provided with a platform 9 for attaching a medical device exterior to the bone 10, the platform 9 mounted at or integrated to the proximal end 20 to project out of the bone 10 when the implant 1 is anchored. Such a medical device may be an external fixation rod, such as a spinal fixation rod, e.g. for spinal fusion. The medical device may e.g. be mounted when the implant 1 is implanted or be mounted post-surgery, for example when the implant 1 has sufficiently integrated and the bone has been sufficiently restored. The platform 9 may be implemented in any manner suitable for the specific implementation. In this example, the platform 9 comprises for example two spaced apart tabs 90,91. The tabs 90,91 project from the proximal end 20 away from the anchoring body 2, and in the space between the tabs 90,91 a fastener for the medical device can be admitted. For example, the fastener can be a rod (not shown) which is clamped in the platform by a screw cap 11 which is screwed into the space defined by the tabs.

The platform 9 is mounted on the proximal end as follows. The platform 9 has a body with an open space 92, which is open at the side of the tabs 90,91 and which is defined by an inside wall 93 which has a shape conforming to a shape of at least a part of the outer surface of the anchoring body at the proximal end 20. The wall 93 has a passage 94 with a diameter large than the diameter of the distal end, but smaller than the diameter of the proximal end. The anchoring body 2 can thus be inserted from the open space side with the distal end 21 leading, until the proximal end 20 is blocked by the passage 94. The platform 9 may then be fixated to the proximal end 20, for example by placing the rod or other object in the open space 92 against the proximal end 20 and screwing the screw cap, thus clamping the proximal end 20 between the wall 93 and the object.

Referring now to FIGS. 6 and 7, a kit of parts for assembling an implant 1 may comprise the anchoring body, the components of the expandable part (either already assembled or as separate parts), the transmission 7 and, optionally other parts. The shown example may be assembled by first positioning the expandable part 3 as well as an actuating element 73 in the space 22, with these elements aligned on the axis a of the anchoring body 2. Subsequently, the rod may be inserted from the distal end 21, such that it passes through the passage 733 and respective ring-shaped links that link the rod to the movable pieces 4, into the bore 26. The cap 8 may then be placed on the distal end 21 to secure the rod relative to the anchoring body 2. The expandable part 3 is put in the non-expanded state by moving the actuating elements 73 in the corresponding position and pushing the movable pieces 4 towards the axis, for example until they are maximally interdigitated. Prior to this, or thereafter, the platform may be mounted as explained earlier The kit or the implant 1 can be provided in a, preferably sterile, package, either alone, together with other components of an implant system (such as pharmaceutically formulation to be applied, bone cement compositions, its surgical toolset, or otherwise) and/or with a medical device. The package may be labelled or provided together with instructions to use the implant 1 in a type surgery, and/or for the treatment of a condition, selected from the group consisting of: vertebral fracture, collapse of vertebral endplates, vertebral height restoration, trauma fracture, or in-vivo implantation in at least one selected from the group consisting of: non-human animal, human, domestic animal, pets, livestock. Other examples may be: internal skeletal fixation, external skeletal fixation, posterior fixation, in combination with pedicle screws and rods system, Lumbar interbody fusion (LIF), Anterior LIF (ALIF), Transforaminal LIF (TLIF), Lateral LIF (LLIF), Posterior LIF (PLIF). Examples of such conditions are: Degenerative disc disease, Spondylolisthesis, Spinal stenosis, Scoliosis, Spinal disc herniation, Discogenic pain, Spinal tumor, Kyphosis, Lordosis.

Referring to FIGS. 8-14, the implant may be used in a method of surgery of a living, human or non-human, mammalian body. As an example of a bone 10, the implant 1 is shown anchored in a human vertebra, which as shown has a vertebral body with endplates 100 and a vertebral pedicle 101. Further indicated in those FIGS. is a cavity 102 in the vertebral body. In this example, the intra-osseous cavity 102 has been pre-prepared to be located close to the surface of the bone on which the external load acts, in this example the vertebral endplate 100. For example, 5 mm or less, such as 4 mm or less, such as 3 mm or less of bone tissue may be present between the top or load bearing surface 5 of the implant and the endplate 100. This allows an elastic or plastic deformation of this tissue by the load bearing surface 5 pushing against the vertebral endplate 100 upon expansion and accordingly allows to reduce the risk of bone fracture or collapse when expanding the implant 1 (e.g. to partially or completely restore the vertebral height). For instance, 1 mm or more, such as 2 mm or more, for example 3 mm of tissue may be present between the top surface 30 and the vertebral endplate. This reduces the risk that the implant 1 pierces through the tissue and becomes exposed during expansion or post-surgery.

Additionally, as illustrated, the distal end 21 can be positioned close to the anterior wall of the vertebra 10. For instance, the implant 1 may be positioned such that there is 1 mm or more, such as 2 mm or more, such as 3 mm or more of space, e.g. with spongy bone material, left between the distal end 21 and the anterior wall. Preferably, this space is 8 mm or less, such as 6 mm or less, for example 5 mm or less. This allows to avoid piercing of the anterior wall by the implant 1. The position of the implant 1 may be determined prior to expansion, for instance, via imaging techniques well known in the art, so as to ensure the implant is fully inside the vertebral body, and e.g. is not in the pedicle.

In such a method an incision may be made in the mammalian body; and the implant 1 be inserted in a bone. As illustrated in FIG. 12, for example a cannula 103 may be pre-prepared in the vertebra, and optionally at the end thereof a cavity be prepared. The implant 1 can be placed with the distal end 21 in the cavity and the proximal end 20 outside the cavity, while the anchoring part 2 is anchored in the part of the bone 10 outside the cavity prior, during or after the distal end 21 is positioned. The expandable part can then be expanded by exerting a moving force on the drive part 6.

As illustrated in FIG. 13, the implant can for example be anchored in the pedicle by rotating the entire implant 1 and thereby screwing the anchoring part 2 in the cannula 103, until the expandable part 3 is at the desired depth and the load supporting surfaces 5 oriented as the medical practitioner deems appropriate. The implant is then in the position and state illustrated in FIGS. 8 and 9 and can be expanded. With the shown example, anchoring the implant 1 and expanding the expandable part 3 may be performed as separate steps. This allows to increase the control over the torque and/or pressure exerted at the interface between the load supporting surface 5 and the bone 10. For example, the implant 1 may be inserted in a pre-made cannula 103 in the bone 10 with the distal end 21 first, until the profiled part 25a of the anchoring body 2 enters the cannula. Up to this point the implant may e.g. be slid, without rotation. Upon further insertion, the anchoring body 2 starts frictionally anchoring in the cannula. In this example by rotating the implant 1 the anchoring part 2 with tread the wall of the cannula 103, and this thread-forming insertion can then be continued until the distal end 21 is at the desired depth in the cannula 103. During this, the implant 1 remains in the non-expanded state. When the implant 1 is at the desired depth and the load supporting surface 5(s) are oriented in the desired direction, a force is exerted on the drive part 6, which as explained above it transferred to the expandable part to expand the implant 1. The implant 1 is then in the expanded state, illustrated in FIGS. 10-11 and 14. As shown, the expansion is obtained by a rotating movement of the drive part 6 in this example, which is transferred to the rod 76 and subsequently transformed in a translational movement of the actuating elements 73 in the longitudinal direction l. This translational movement is transformed by the actuating elements 73 in the movement of the movable pieces 4 in the direction of expansion d.

In the foregoing specification, the invention has been described with reference to specific examples of embodiments of the invention. It will, however, be evident that various modifications and changes may be made therein without departing from the scope of the invention as set forth in the appended claims, and that the examples are not intended to be limiting.

For example, although in the example an implant for spinal surgery has been described, the implant can be implemented to be used in other bones. Furthermore, if the platform is present this may be an anchor for other medical devices. For instance, this can be implemented as an anchor for transfixation pins to which a connecting bar may be fixated in external or internal skeletal fixation. The platform can alternatively or additionally be implemented as stem for, for example, an artificial femoral, hip or shoulder joint. Likewise, the platform can be implemented as an anchor for an electronic medical device or for a medical device releasing a pharmaceutically active component.

Also, the movable pieces, and more generally the parts of implant may be made of any suitable biocompatible material. The material may for example contain a material out of the group consisting of: metals, metal compounds, metal alloys, metal composites, polymers, ceramics and combinations of materials of this group. The biocompatible material can contain a metal out of the group consisting of: titanium, tantalum, niobium, stainless steel, cobalt chrome alloys, zirconia, or a compound, alloy or composite thereof. Other suitable biocompatible materials can contain a polymer out of the group consisting of polyaryletherketone, polyether ether ketone, polyetherketoneketone. In this respect, all parts of the implant may be made of the same material or different parts may be made of different materials.

One, or more than one, or all of the parts may be non-degradable in-vivo or in-situ. This allows a permanent structure. For example, the anchoring part may be made of a non-degradable metal containing material, whereas e.g. a movable piece made be made of a degradable material. Alternatively or additionally, one, or more than one, or all of the parts may be bio-degradable in-vivo. This allows e.g. to place a temporary implant, or an implant with temporary parts, without requiring surgery to remove the implant. Also, for instance, the bio-degradable degradable part may fill a gap between a non-degradable part and tissue to be regrown, such as bone. This allows e.g. placing an implant at a location in a space larger than the implant, expanding the implant such that the degradable part bridges the space between the non-degradable part and the edge of the gap. The degradable part can then disappear while the gap fills, e.g. by tissue regrowth.

The anchoring body 2 may for example be made from materials different from the movable pieces 4. This allows them to have different properties, such as a rigid anchoring body 2 and a flexible movable piece 4 or vice-versa. One, or more than one, or all of the anchoring body 2 and movable pieces 4 may be non-degradable in-vivo or in-situ. This allows a permanent implant, e.g. suitable for an implant which serves as an anchor for a prosthesis.

Alternatively or additionally, one, or more than one, or all of the anchoring body 2 and movable pieces 4 may be bio-degradable in-vivo. This allows e.g. to place a temporary implant without requiring surgery to remove the implant 1, or an implant with temporary parts. For example, the movable pieces 4 may be biodegradable while the anchoring body, or at least a core thereof, is made of a non-degradable material, such as a non-corrosive metal. This allows to anchor the implant 1 during the healing period and if the platform 9 is present keep the platform 9 anchored after the healing period even after the expandable part 3 has decomposed. In addition, for example an outer sleeve of the anchoring body may be biodegradable while the core is made of a stiff, non-degradable material (e.g. Ti or biocompatible Ti-alloys). This similarly allows to firmly anchor the implant 1 during healing while, due to the degrading of the outer sleeve, after healing the anchoring body 2 be easily removed. In such a case for example the expandable part can be left in the bone, e.g. when it has completely osseo-integrated therein.

In this, for instance, the non-degradable parts to be removed after healing, may have a closed-surface to avoid integration, such as osseo-integration, in the bone 10 while the degradable parts have an open, porous surface to allow osseo-integration. Alternatively, the non-degradable parts may integrate into the bone 10 and e.g. osseo-integrate. For example, the anchoring body 2 may be biodegradable. This allows to initially anchor the implant 1. When the anchoring body 2 degrade and the movable pieces 4 integrate, e.g. by osseo-integration, the adherence between the integrated parts and the bone 10 can take over the anchoring function. This allows e.g. to reduce prolonged locally high pressure caused by the anchoring body 2 pressing into the bone 10 and, without being bound to theory, is believed to reduce secondary complications post-surgery.

Furthermore, one or more of the anchoring body 2, the platform 9, the movable piece 4, the cap 8, the actuating elements 73, the rod 76 or other elements may be a mono-lithic body.

Likewise, where a movement of an object is described (e.g. relative to another object) it will be apparent that, unless explicitly specified otherwise, this is a relative move-ment, and accordingly depending on the chosen reference frame, the object may be moving relative to an observer while the other object is static, the other object may be moving while the object is static relative to the observer or both objects may be moving, but differently, relative to the observer. Moreover, the terms "front," "back," "top," "bot-tom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

However, other modifications, variations and alternatives are also possible. The specifications and drawings are, accordingly, to be regarded in an illustrative rather than in a restrictive sense.

In the claims, any reference signs placed between paren-theses shall not be construed as limiting the claim. The word 'comprising' does not exclude the presence of other ele-ments or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements The mere fact that certain measures are recited in mutually different claims does not indicate that a combination of these measures cannot be used to advantage.

LIST OF REFERENCE NUMBERS l longitudinal direction
a axis r radial direction
d direction of expansion
1 expandable implant
2 anchoring body
3 expandable part
4 movable piece
5 load supporting surface
6 drive part
7 transmission
8 cap
9 platform
10 bone
20 proximal end
21 distal end
22 space
23 opening
24 prongs
25 outer surface
26 bore
27 thread
28 recess
40 inwards facing side
41 porous layer
42 porous inside
70 driving part
71 rod
72 mechanical actuator
73 elements
74 mounting position
730 inclined plane
731 base
732 passage
80 conical tip
81 threaded bore
82 recess
90,91 tabs
92 space
93 wall
94 passage
100 vertebral end plate
101 pedicle
102 cavity

The invention claimed is:

1. An expandable implant which is implantable in-vivo in an intra-osseous cavity of a bone, of a human or non-human mammal, the implant comprising:
   an anchoring body having a distal end and a proximal end, in a longitudinal direction from the distal end towards the proximal end at a distance from the distal end, for anchoring the distal end relative to a part of the bone outside the cavity;
   an expandable part to be admitted in the intra-osseous cavity, which expandable part:
   is fixated to the anchoring body,
   has an expanded state and a non-expanded state, and
   comprises a movable piece with a load supporting surface for supporting a wall of the cavity against a load acting on the bone, which movable piece is movable from an initial position in the non-expanded, in a direction of expansion away from the anchoring body and perpen-dicular to the longitudinal direction, to bring the load supporting surface state to an expanded position in the expanded state in which the load supporting surface abuts to the wall;
   a drive part which is movable relative to the proximal end of the anchoring body; and a transmission extending between the drive part and the expandable part, the transmission engaging on the load supporting surface for transferring at least a part of a force exerted on the drive part to move the drive part relative to the proximal end of the anchoring body to the load supporting surface and thereby actuate movement of the load supporting surface in the direction of expansion;

wherein the anchoring body is an elongate body, with a bore, extending from the proximal end to the distal end, and the transmission extends through the bore;

wherein the transmission comprises a rod, which can be moved relative to the bore; and wherein the rod is rotatable relative to, and in, the bore around a longitudinal axis parallel to the longitudinal direction but not translationally movable in the longitudinal direction relative to the bore.

2. An expandable implant which is implantable in-vivo in an intra-osseous cavity of a bone, of a human or non-human mammal, the implant comprising:

an anchoring body having a distal end and a proximal end, in a longitudinal direction from the distal end towards the proximal end at a distance from the distal end, for anchoring the distal end relative to a part of the bone outside the cavity;

an expandable part to be admitted in the intra-osseous cavity, which expandable part:

is fixated to the anchoring body, has an expanded state and a non-expanded state, and comprises a movable piece with a load supporting surface for supporting a wall of the cavity against a load acting on the bone, which movable piece is movable from an initial position in the non-expanded, in a direction of expansion away from the anchoring body and perpendicular to the longitudinal direction, to bring the load supporting surface state to an expanded position in the expanded state in which the load supporting surface abuts to the wall;

a drive part which is movable relative to the proximal end of the anchoring body; and a transmission extending between the drive part and the expandable part, the transmission engaging on the load supporting surface for transferring at least a part of a force exerted on the drive part to move the drive part relative to the proximal end of the anchoring body to the load supporting surface and thereby actuate movement of the load supporting surface in the direction of expansion;

wherein the anchoring body is an elongate body, with a bore, extending from the proximal end to the distal end, and the transmission extends through the bore;

wherein the movable piece comprises an inward facing side, facing away from, and preferably opposite to the load supporting surface;

wherein the transmission comprises a mechanical actuator located below the movable piece, which engages with the inward facing side, and a driving part extending through the bore arranged to drive the mechanical actuator;

wherein the mechanical actuator comprises at least two elements mounted on the driving part at in the longitudinal direction spaced apart positions, and the positions being movable towards each other in the longitudinal direction by a motion of the driving part, the elements when the positions are moved pushing the movable piece in the direction of expansion; and wherein the elements have a conical shape and are oriented with their axial direction extending in the longitudinal direction, and the bases of the conical shapes facing away from each other.

3. An expandable implant which is implantable in-vivo in an intra-osseous cavity of a bone, of a human or non-human mammal, the implant comprising:

an anchoring body having a distal end and a proximal end, in a longitudinal direction from the distal end towards the proximal end at a distance from the distal end, for anchoring the distal end relative to a part of the bone outside the cavity;

an expandable part to be admitted in the intra-osseous cavity, which expandable part:

is fixated to the anchoring body, has an expanded state and a non-expanded state, and comprises a movable piece with a load supporting surface for supporting a wall of the cavity against a load acting on the bone, which movable piece is movable from an initial position in the non-expanded, in a direction of expansion away from the anchoring body and perpendicular to the longitudinal direction, to bring the load supporting surface state to an expanded position in the expanded state in which the load supporting surface abuts to the wall;

a drive part which is movable relative to the proximal end of the anchoring body; and a transmission extending between the drive part and the expandable part, the transmission engaging on the load supporting surface for transferring at least a part of a force exerted on the drive part to move the drive part relative to the proximal end of the anchoring body to the load supporting surface and thereby actuate movement of the load supporting surface in the direction of expansion;

wherein the anchoring body is an elongate body, with a bore, extending from the proximal end to the distal end, and the transmission extends through the bore;

wherein the movable piece comprises an inward facing side, facing away from, and preferably opposite to the load supporting surface;

wherein the transmission comprises a mechanical actuator located below the movable piece, which engages with the inward facing side, and a driving part extending through the bore arranged to drive the mechanical actuator;

wherein the mechanical actuator comprises at least two elements mounted on the driving part at in the longitudinal direction spaced apart positions, and the positions being movable towards each other in the longitudinal direction by a motion of the driving part, the elements when the positions are moved pushing the movable piece in the direction of expansion; and wherein the elements have an inclined plane, inclined relative to the longitudinal direction, the inclined plane contacting the inwards facing side and oriented to slide over the inwards facing side to push the movable piece when the positions are moved towards each other.

4. An expandable implant which is implantable in-vivo in an intra-osseous cavity of a bone, of a human or non-human mammal, the implant comprising:

an anchoring body having a distal end and a proximal end, in a longitudinal direction from the distal end towards the proximal end at a distance from the distal end, for anchoring the distal end relative to a part of the bone outside the cavity;

an expandable part to be admitted in the intra-osseous cavity, which expandable part: is fixated to the anchoring body, has an expanded state and a non-expanded state, and comprises a movable piece with a load supporting surface for supporting a wall of the cavity against a load acting on the bone, which movable piece is movable from an initial position in the non-expanded, in a direction of expansion away from the anchoring body and perpendicular to the longitudinal direction, to bring the load supporting surface state to an expanded position in the expanded state in which the load supporting surface abuts to the wall;

a drive part which is movable relative to the proximal end of the anchoring body; and a transmission extending between the drive part and the expandable part, the transmission engaging on the load supporting surface for transferring at least a part of a force exerted on the drive part to move the drive part relative to the proximal end of the anchoring body to the load supporting surface and thereby actuate movement of the load supporting surface in the direction of expansion;

wherein the expandable part is at least partially admitted in a space in the anchoring body located at the distal end, the space having an opening to allow the movable piece to move outwards in the direction of expansion, in which:

the distal end is shaped as a slotted tube;

the space is formed by a slot of the slotted tube in which the expandable part is located, the slot having an opening extending parallel to the longitudinal direction; and the movable piece is in the initial position at least partly recessed in the slot and movable through the opening to the expanded position; and a mechanical actuator comprises at least two elements mounted on the driving part at spaced apart positions in the longitudinal direction, and the positions being movable towards each other in the longitudinal direction by a motion of the driving part, the elements pushing the movable piece in the direction of expansion when the positions are moved; and of which the at least two elements comprise a stationary element at one of a proximal end side or a distal end side of the space and is an element of which the position is stationary, and at least one other elements is formed by a separate piece located in the space, the separate piece being movable in the space in the longitudinal direction.

5. An expandable implant which is implantable in-vivo in an intra-osseous cavity of a bone, of a human or non-human mammal, the implant comprising:

an anchoring body having a distal end and a proximal end, in a longitudinal direction from the distal end towards the proximal end at a distance from the distal end, for anchoring the distal end relative to a part of the bone outside the cavity, wherein the anchoring body is an elongate body, with a bore, extending from the proximal end to the distal end, and a transmission extends through the bore;

an expandable part to be admitted in the intra-osseous cavity, which expandable part:

is fixated to the anchoring body, has an expanded state and a non-expanded state, and comprises a movable piece with a load supporting surface for supporting a wall of the cavity against a load acting on the bone, which movable piece is movable from an initial position in the non-expanded, in a direction of expansion away from the anchoring body and perpendicular to the longitudinal direction, to bring the load supporting surface state to an expanded position in the expanded state in which the load supporting surface abuts to the wall;

a drive part which is movable relative to the proximal end of the anchoring body; and a transmission extending between the drive part and the expandable part, the transmission engaging on the load supporting surface for transferring at least a part of a force exerted on the drive part to move the drive part relative to the proximal end of the anchoring body to the load supporting surface and thereby actuate movement of the load supporting surface in the direction of expansion; and wherein the expandable part is at least partially admitted in a space in the anchoring body located at the distal end, the space having an opening to allow the movable piece to move outwards in the direction of expansion, in which:

the distal end is shaped as a slotted tube;

the space is formed by a slot of the slotted tube in which the expandable part is located, the slot having an opening extending parallel to the longitudinal direction; and the movable piece is in the initial position at least partly recessed in the slot and movable through the opening to the expanded position, wherein the movable piece comprises an inward facing side, facing away from, and preferably opposite to the load supporting surface, and the transmission comprises:

a mechanical actuator located below the movable piece, which engages with the inward facing side, and a driving part extending through the bore arranged to drive the mechanical actuator, wherein the mechanical actuator comprises at least two elements mounted on the driving part at in the longitudinal direction spaced apart positions, and the positions being movable towards each other in the longitudinal direction by a motion of the driving part, the elements when the positions are moved pushing the movable piece in the direction of expansion.

6. The implant of claim 5, wherein the anchoring body has a longitudinal axis parallel to the longitudinal direction, and the driving part is rotatable relative to the anchoring body around the longitudinal axis.

7. The implant of claim 5, wherein the transmission comprises a rod, which can be moved relative to the bore.

8. The implant of claim 5, wherein:

a rod extends through the at least two elements, and engages with at least one of the at least two elements to transform a motion of the rod in a movement of the engagement positions.

9. The implant of claim 1, wherein the outside of the anchoring body has a friction enhancing profile for holding the implant in the part of the bone.

10. The implant of claim 1, comprising a platform for attaching a medical device exterior to the bone, the platform mounted at or integrated to the proximal end and when the implant is anchored projecting out of the bone.

11. The implant of claim 1, wherein the implant is for implantation into a bone in the group consisting of: a vertebra, such as lumbar vertebra, thoracic vertebra and or sacral vertebra.

12. The implant of claim 1, wherein the implant is insertable in the human or non-human mammal by driving the anchoring body in the longitudinal direction into the bone.

13. The implant of claim 1, wherein the anchoring body has a longitudinal axis extending from the proximal end towards the distal end, and the anchoring body is rotationally movable around the longitudinal axis relative to the bone to anchor the implant and orient the load supporting surface, and the movable piece is movable outwards from the anchoring body in a radial direction perpendicular to the longitudinal axis to expand after anchoring.

14. The implant of claim 1, provided in a sterile package labelled or provided together with instructions to use the implant in a type surgery, and/or for the treatment of a condition, selected from the group consisting of: vertebral fracture, collapse of vertebral end-plates, vertebral height restoration, trauma fracture, or in-vivo implantation in at least one selected from the group consisting of: non-human animal, human, domestic animal, pets, livestock.

* * * * *